United States Patent
Lu

(10) Patent No.: US 12,023,380 B2
(45) Date of Patent: Jul. 2, 2024

(54) COMBINED CANCER THERAPY WITH IMMUNE CHECKPOINT MODULATORS AND FERMENTATION PRODUCTS BY SYMBIOTIC MICROBIOTA

(71) Applicant: MICROBIO CO. LTD., Taipei (TW)

(72) Inventor: Kung-Ming Lu, Taipei (TW)

(73) Assignee: MICROBIO CO. LTD., Taipei (TW)

( * ) Notice: Subject to any disclaimer, the term of this patent is extended or adjusted under 35 U.S.C. 154(b) by 480 days.

(21) Appl. No.: 16/953,026

(22) Filed: Nov. 19, 2020

(65) Prior Publication Data

US 2021/0069327 A1 Mar. 11, 2021

Related U.S. Application Data

(62) Division of application No. 15/473,981, filed on Mar. 30, 2017, now Pat. No. 10,869,923.

(60) Provisional application No. 62/315,259, filed on Mar. 30, 2016.

(51) Int. Cl.
| | |
|---|---|
| *A61K 39/395* | (2006.01) |
| *A61K 9/00* | (2006.01) |
| *A61K 31/19* | (2006.01) |
| *A61K 31/191* | (2006.01) |
| *A61K 31/197* | (2006.01) |
| *A61K 31/198* | (2006.01) |
| *A61K 36/48* | (2006.01) |
| *A61K 39/00* | (2006.01) |
| *A61K 45/06* | (2006.01) |
| *C07K 16/28* | (2006.01) |
| *C12P 7/54* | (2006.01) |
| *C12P 7/56* | (2006.01) |
| *C12P 13/00* | (2006.01) |

(52) U.S. Cl.
CPC ........ *A61K 39/3955* (2013.01); *A61K 9/0019* (2013.01); *A61K 9/0053* (2013.01); *A61K 9/0095* (2013.01); *A61K 31/19* (2013.01); *A61K 31/191* (2013.01); *A61K 31/197* (2013.01); *A61K 31/198* (2013.01); *A61K 36/48* (2013.01); *A61K 45/06* (2013.01); *C07K 16/2803* (2013.01); *C07K 16/2818* (2013.01); *C12P 7/54* (2013.01); *C12P 7/56* (2013.01); *C12P 13/002* (2013.01); *A61K 2039/505* (2013.01); *A61K 2039/542* (2013.01); *A61K 2236/19* (2013.01); *C07K 2317/76* (2013.01)

(58) Field of Classification Search
CPC ........ A61K 2039/505; A61K 2039/542; A61K 2236/19; A61K 2300/00; A61K 31/19; A61K 31/191; A61K 31/197; A61K 31/198; A61K 36/48; A61K 39/3955; A61K 45/06; A61K 9/0019; A61K 9/0053; A61K 9/0095; A61P 35/00; A61P 43/00; C07K 16/2803; C07K 16/2818; C07K 2317/76; C12P 13/002; C12P 7/54; C12P 7/56

See application file for complete search history.

(56) References Cited

U.S. PATENT DOCUMENTS

| | | | |
|---|---|---|---|
| 10,869,923 B2 * | 12/2020 | Lu | ........ C07K 16/2818 |
| 2004/0219237 A1 | 11/2004 | Lu | |
| 2005/0222248 A1 | 10/2005 | Joannou | |
| 2013/0323249 A1 | 12/2013 | Zhou et al. | |
| 2014/0341920 A1 * | 11/2014 | Noelle | ........ C07K 14/70532 |
| | | | 424/141.1 |

FOREIGN PATENT DOCUMENTS

| | | | | |
|---|---|---|---|---|
| EP | 1243274 A2 | 9/2002 | | |
| JP | 2003-335695 A | 11/2003 | | |
| WO | WO-2005032568 A1 * | 4/2005 | ........ | A23L 27/50 |
| WO | WO 2015/069770 A1 | 5/2015 | | |
| WO | WO 2015/095811 A2 | 6/2015 | | |

OTHER PUBLICATIONS

Lai et al., Effect of lactic fermentation on the total phenolic, saponin and phytic acid contents as well as anti-colon cancer cell proliferation activity of soymilk. J Biosci Bioeng. May 2013; 115(5):552-6. Epub Jan. 4, 2013.

Seo et al., Identification of Bacillus cereus in a chungkukjang that showed high anticancer effects against AGS human gastric adenocarcinoma cells. J Med Food. Dec. 2009;12(6):1274-80.

* cited by examiner

*Primary Examiner* — Blaine Lankford

(74) *Attorney, Agent, or Firm* — Mintz, Levin, Cohn, Ferris, Glovsky and Popeo, P.C.

(57) ABSTRACT

Combined therapy of cancer using an immune check point modulators (e.g., an immune checkpoint inhibitor) and a fermented product, which may be prepared using symbiotic microbiota.

28 Claims, 26 Drawing Sheets

COMBINED CANCER THERAPY WITH IMMUNE CHECKPOINT MODULATORS AND FERMENTATION PRODUCTS BY SYMBIOTIC MICROBIOTA

RELATED APPLICATION

This application is a divisional of, and claims the benefit of and priority to, U.S. patent application Ser. No. 15/473,981, filed Mar. 30, 2017, which claims the benefit of U.S. provisional application No. 62/315,259, filed Mar. 30, 2016 under 35 U.S.C. § 119, the entire contents of each of which are herein incorporated by reference.

BACKGROUND OF THE INVENTION

Immune checkpoints are molecules that regulate signaling pathways in the immune system, thereby regulating immune cell activities in immune responses. Many cancer cells can escape immune surveillance via inhibiting T cell activation. Since 2010, immune checkpoints have been increasingly considered as new targets for cancer immunotherapy. A number of checkpoint modulators, e.g., Yervoy® (ipilimumab), Keytruda® (pembrolizumab), and Opdivo® (nivolumab), have been demonstrated in clinical trials as being effective in suppressing cancer cell growth.

Fermentation is a metabolic process that converts sugar to acids, gases or alcohol by microorganisms, such as yeast and bacteria, or by oxygen-starved muscle cells, as in the case of lactic acid fermentation. In food processing, fermentation is the conversion of carbohydrates to alcohols and carbon dioxide or organic acids using yeasts, bacteria, or a combination thereof, under anaerobic conditions. Metabolites generated in a fermentation process often confer benefits to health.

SUMMARY OF THE INVENTION

The present disclosure is based on the unexpected synergistic effects of a combination of an immune check point modulator (e.g., an anti-PD1 antibody) and a fermented soybean composition on suppressing cancer growth.

Accordingly, one aspect of the present disclosure provides a method for treating cancer, comprising: (i) administering to a subject in need thereof an effective amount of an immune checkpoint modulator (e.g., an immune checkpoint inhibitor); and (ii) administering to the subject a fermented composition (e.g., a fermented soybean composition), which comprises multiple metabolites that are generated via fermentation of a legume plant, a portion thereof, or an extract thereof by one or more suitable microorganisms.

In another aspect, the present disclosure provides a method for treating cancer, comprising administering to a subject in need thereof an effective amount of a fermented soybean composition as described herein, wherein the subject has undergone or is undergoing an anti-cancer therapy that involves an immune checkpoint modulator (e.g., an immune checkpoint inhibitor).

In any of the methods described herein, the fermented composition can be administered by oral administration or by intravenous administration. In some examples, the fermented composition can be in liquid form. In some embodiments, the fermented composition may comprise multiple metabolites that are generated via fermentation of a legume plant (e.g., soybean), a portion thereof (e.g., seeds), or an extract thereof by a yeast, a *lactobacillus*, or a combination thereof. The fermented composition maybe administered before, after, or concurrently with the administration of the immune checkpoint modulator.

In some embodiments, the fermented composition may comprise a combination of (e.g., two or more) of lactic acid, acetic acid, and 3-aminoisobutyric acid. In one example, the fermented composition comprise lactic acid at 5-20% by weight, acetic acid at less than 5% by weight, and 3-aminoisobutyric acid at less than 5% by weight.

In some examples, the fermented composition may be prepared by a process comprising: (i) growing the yeast, the *lactobacillus*, or the combination thereof in a medium comprising a legume plant (e.g., soybean), a portion thereof (e.g., seeds), or an extract thereof under conditions allowing for fermentation of the soybean or the extract thereof; and (ii) collecting the fermented composition obtained from step (i). Optionally, the preparation process may further comprise filtering the fermented composition, sterilizing the fermented composition, and/or concentrating the fermented composition.

The immune checkpoint modulator for use in any of the methods described herein can be an modulator (e.g., an inhibitor) of an immune checkpoint molecule, which may be PD-1, CD28, CTLA-4, CD137, CD40, CD134, ICOS, KIR, LAGS, CD27, TIM-3, BTLA, GITR, TIGIT, CD96, CD226, KIR2DL, VISTA, HLLA2, TLIA, DNAM-1, CEACAM1, CD155, IDO (e.g., IDO1), TGF-beta, IL-10, IL-2, IL-15, CSF-1, IL-6, and adenosine A2A receptor (A2AR), or a ligand thereof. In some embodiments, the immune checkpoint modulator is an antibody specific to the immune checkpoint, or a ligand thereof, for example, an antibody specific to PD1 or a ligand thereof (PDL1 or PDL2). In some examples, the antibody can be a human antibody, a humanized antibody, or a chimeric antibody.

Exemplary cancers to be treated by the method described herein include, but are not limited to, colon cancer, lung cancer, breast cancer, pancreatic cancer, skin cancer, brain cancer, ovarian cancer, kidney cancer, stomach cancer, head and neck cancer, esophageal cancer, bladder cancer, rectal cancer, bone cancer, uterine cancer, prostate cancer, and hematological malignancy.

Further, the present disclosure features a kit comprising (i) one or more of the immune checkpoint modulators as described herein, and (ii) a fermented soybean composition as described herein.

Also within the scope of the present disclosure are (i) pharmaceutical compositions for use in treating cancer, e.g., those described herein, the pharmaceutical composition comprising an immune checkpoint modulator and a fermented soybean composition as described herein; and uses of the combination of the immune checkpoint modulator and fermented soybean composition for manufacturing a medicament for use in treating cancer.

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

Figure 1A:
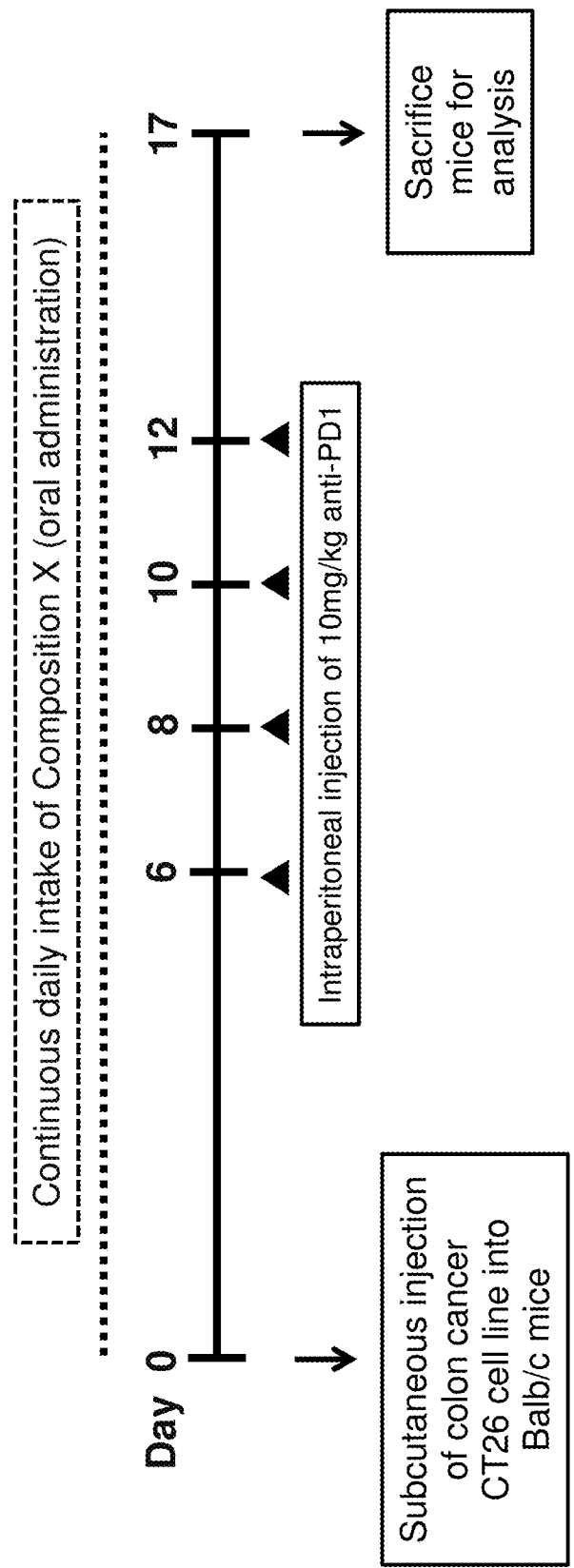
FIG. 1A is a schematic illustration of an experimental design for studying the effect of a combination of an anti-PD1 antibody and a fermented composition (Composition X) via oral administration in a colon cancer mouse model. The mice were concurrently transplanted with colon cancer CT26 cells and treated with of the fermented composition.

Immune checkpoint modulators have been shown to effectively inhibit cancer cell growth in many studies. The studies provided in the present disclosure demonstrate, surprisingly, that fermented soybean compositions, for example, an exemplary soybean fermented composition, Composition X described herein, successfully enhanced the anti-cancer effect of an immune checkpoint modulator (e.g., an immune checkpoint inhibitor such as an anti-PD1 antibody). In some instances, the co-use of the immune checkpoint modulator and the fermented soybean composition exhibited synergistic effects in suppressing cancer growth in an animal cancer model. Without being bound by theory, the results of this study show that the fermented composition may facilitate the immune checkpoint inhibitor to modulate intestinal microbiota, which was reported in the art as involved in cancer development. These unexpected results indicate that the fermented soybean composition can be co-used with one or more immune checkpoint modulators such as inhibitors to more effectively treat cancer.

Accordingly, provided herein are combined cancer therapies involving the co-use of immune checkpoint modulators and fermented soybean compositions and kits for such uses.

I. Agents for Combined Cancer Therapy

The combined cancer therapies described herein involves the use of immune checkpoint modulators and fermented compositions such as fermented soybean compositions as active agents.

(a) Immune Checkpoint Modulators

Immune checkpoint proteins refer to molecules involved in a plethora of regulatory pathways that regulate (e.g., either turning up or turning down a signal of) the immune system to maintain self-tolerance and to modulate the duration and amplitude of physiological immune responses in peripheral tissues in order to minimize collateral tissue damage. Typically, immune checkpoint proteins are dysregulated by cancer cells (e.g., tumors). Without wishing to be bound by any particular theory, immune checkpoint proteins can be targeted with modulators (activators or inhibitors) as an anti-cancer therapy, for example as described by Pardoll et al., Nature Reviews Cancer, 12: 252-264, 2012.

The immune cell signaling pathways can be mediated by one or more of the following exemplary receptor/ligand pairs on cells: PD1/PDL1, PD1/PDL2, CD28/B7-1 (CD80), CD28/B7-2 (CD86), CTLA4/B7-1(CD80), CILA4/B7-2 (CD86), 4-1BB (CD137)/4-1BBL (CD137L), ICOS/B7RP1, CD40/CD40L, Herpesvirus entry mediator (HVEM)/B- and T-lymphocyte attenuator (BTLA); OX40/OX40L, CD27/CD70, GITR/GITRL, KIR/MHC, Lymphocyte-activation gene 3 (LAG3 or CD223)/MHC, Hepatitis A virus cellular receptor 2 (HAVCR2; also known as T-cell immunoglobulin and mucin-domain containing-3 (TIM3))/TIM3 ligand, T cell immunoreceptor with Ig and ITIM domains (TIGIT)/CD96, and TIGIT/CD226. The immune cell signaling pathways can also be mediated by one or more of the following exemplary cytokines/chemokines and their cognate cell-surface receptors: interleukin 2 (IL-2)/CD122, adenosine/adenosine A2A receptor (A2AR), interleukin 6 (IL-6)/IL6R (CD126), interleukin 10(IL-10)/IL-10R, interleukin 15(IL-15)/IL-15R, transforming growth factor β (TGFβ)/TGFβR, and Macrophage colony-stimulating factor 1 (CSF-1)/CSF-1R. Other immune checkpoints include, but are not limited to, KIR2DL, VISTA, HLLA2, TLIA, DNAM-1, CEACAM1, CD155, and indoleamine 2,3-dioxygenase (IDO), such as IDO1. Any of the immune checkpoint molecules described above can be a target for anti-cancer therapy as described herein.

As used herein, "immune checkpoint modulator" refers to an agent that alters the activity of an immune checkpoint protein (e.g., any of those described herein) in a cell relative to a control vehicle. The term "modulator" is used herein in the broadest sense, and includes any molecule that partially or fully alters a signaling pathway regulated by one or more immune checkpoint molecules, including the signaling pathways mediated by the molecules described herein.

In some instances, an immune checkpoint modulator is an inhibitor of a checkpoint molecule that reduces, slows, halts, and/or prevents the activity mediated by that checkpoint molecule. The term "inhibitor" is used herein in the broadest sense, and includes any molecule that partially or fully blocks, inhibits, or neutralizes a signaling pathway regulated by one or more immune checkpoint molecules, including the modulatory pathways mediated by the molecules described herein. Suitable inhibitory molecules specifically include antagonist antibodies or antibody fragments, fragments or amino acid sequence variants of native polypeptides, peptides, antisense oligonucleotides, small organic molecules, recombinant proteins or peptides, etc.

In other instances, an immune checkpoint modulator is an activator of a checkpoint molecule that enhances and improves the activity mediated by that checkpoint molecule. The term "activator" is used herein in the broadest sense, and includes any molecule that enhances a signaling pathway regulated by one or more immune checkpoint molecules, including the signaling pathways mediated by the molecules described herein. Suitable activators include agonistic antibodies or antibody fragments, small organic molecules, recombinant proteins or peptides, etc. In some instances, the activator can be an agonistic antibody of a checkpoint protein, e.g., MEDI0562 (a humanized OX40 agonistic antibody), MEDI6469 (a murine OX4 agonist); and MEDI6383 (an OX40 agonist).

Methods for identifying such modulators are well known in the art. For example, a candidate modulator can be brought in contact with a suitable immune checkpoint target and the intensity of the signaling mediated by that immune checkpoint can be measured by a conventional assay. A detectable change in the signaling in the presence of the candidate modulator as relative to a blank control indicates that the candidate modulator possesses the regulatory activity of the immune checkpoint molecule.

An immune checkpoint modulator as described herein can be an inhibitory agent that interferes with the signaling in an immune cell that is mediated by an immune checkpoint protein, for example, either by decreasing transcription or translation of checkpoint protein-encoding nucleic acid, or by inhibiting or blocking the checkpoint protein activity, or both. Examples of immune checkpoint inhibitors include, but are not limited to, antisense polynucleotides, interfering RNAs, catalytic RNAs, RNA-DNA chimeras, checkpoint protein-specific aptamers, anti-checkpoint protein antibodies (e.g., full-length antibodies or antigen-binding fragments thereof), checkpoint-binding small molecules, checkpoint-binding peptides, and other polypeptides that specifically bind a checkpoint protein (including, but not limited to, checkpoint-binding fragments of its cognate ligand, which may optionally be fused to one or more additional domains), such that the interaction between the checkpoint modulator and the checkpoint protein results in a reduction or cessation of the checkpoint protein activity or expression. It will be understood by one of ordinary skill in the art that in some instances, a checkpoint protein modulator can antagonize or neutralize one checkpoint protein activity without affecting another checkpoint protein activity. For example, a desirable checkpoint modulator for use in certain of the methods herein can be a checkpoint modulator that disrupts binding interaction between the checkpoint protein and one cognate ligand without affecting or minimally affecting the interaction between the checkpoint protein and another cognate ligand, if any.

The immune checkpoint modulators as described herein may reduce the intensity of the signaling mediated by a checkpoint protein in immune cells by at least 20% or more, e.g., 30%, 40%, 50%, 60%, 70%, 80%, 90%, 95% or above. The regulatory activity of such a modulator against the checkpoint protein can be determined by conventional methods.

Anti-Checkpoint Antibodies

In some embodiments, the immune checkpoint modulator for use in the combined anti-cancer therapy as described herein is an antibody that specifically binds to an immune checkpoint molecule and inhibits its bioactivity, e.g., via interfering its binding to the cognate ligand. As used herein, the term "antibody" as includes but is not limited to polyclonal, monoclonal, humanized, chimeric, Fab fragments, Fv fragments, F(ab') fragments and F(ab')2 fragments, as well as single chain antibodies (scFv), fusion proteins and other synthetic proteins which comprise the antigen-binding site of the antibody.

Any of the antibodies that suppress the activity of an immune checkpoint protein may be prepared by conventional methods known in the art or methods disclosed herein.

In some embodiments, antibodies specific to a target antigen (an immune checkpoint protein such as PD1, PDL1, PDL2, CTLA4 and any others described herein) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., *In Vitro,* 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce monoclonal antibodies specific to an immune checkpoint protein as described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with a signal pathway (e.g., an inhibitory signal pathway) mediated by an immune checkpoint molecule. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the checkpoint signaling pathway. It will be apparent to one of skill in the art that one or more polynucleotide changes can be made to the antibody and still maintain its binding specificity to the target antigen.

In some examples, the anti-checkpoint antibodies described herein can be fully human antibodies. Full human antibodies can be obtained by using commercially available animals (e.g., mice) that have been engineered to express specific human immunoglobulin proteins. Transgenic animals that are designed to produce a more desirable (e.g., fully human antibodies) or more robust immune response may also be used for generation of humanized or human antibodies. Examples of such technology are XenoMouse™ from Amgen, Inc. (Fremont, Calif.) and HuMAb-Mouse™ and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455, and. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibody specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

In other examples, the anti-checkpoint antibodies are humanized antibodies. Humanized antibodies refer to antibodies derived from non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation. Methods for constructing humanized antibodies are also well known in the art. See, e.g., Queen et al., Proc. Natl. Acad. Sci. USA, 86:10029-10033 (1989).

In some embodiments, the checkpoint regulatory antibodies such as checkpoint inhibitory can be chimeric antibodies. Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

In other embodiments, the checkpoint regulatory antibodies such as inhibitory antibodies can be single-chain antibody fragments (scFv). A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to an immune checkpoint protein, which can be identified from the library following routine procedures. Positive clones can be subjected to further screening to identify those that inhibit activity of the immune checkpoint protein.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the immune checkpoint protein have been replaced (swapped) with sequences from a closely related, but antigenically distinct protein. By assessing binding of the antibody to the mutant checkpoint polypeptide, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Nucleic acids encoding the heavy and light chain of an anti-checkpoint antibody as described herein can be cloned into one expression vector, each nucleotide sequence being in operable linkage to a suitable promoter. In one example, each of the nucleotide sequences encoding the heavy chain and light chain is in operable linkage to a distinct prompter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., Cell, 49:603-612 (1987); Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells transactivator or repressor fusion protein, which in some instances can be toxic to cells (Gossen et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-checkpoint antibody, as also described herein. The recombinant expression vector can be introduced into a suitable host cell (e.g., a dhfr-CHO cell) by a conventional method, e.g, calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-checkpoint antibody and the other encoding the light chain of the anti-checkpoint antibody. Both of the two recombinant expression vectors can be introduced into a suitable host cell (e.g., dhfr-CHO cell) by a conventional method, e.g., calcium phosphate-mediated transfection. Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-checkpoint polypeptide antibody as described herein, vectors (e.g., expression vectors) containing such; and host cells comprising the vectors are within the scope of the present disclosure.

Other Immune Checkpoint Modulators

In some embodiments, the checkpoint modulator is an interfering RNA such as a small interfering RNA (siRNA) short hairpin RNA (shRNA). In some embodiments, the checkpoint modulator is a small interfering RNA (siRNA) that binds to the mRNA of the checkpoint protein and blocks its translation or degrades the mRNA via RNA interference. Exemplary small interfering RNAs are described by Hannon et al., Nature, 418 (6894): 244-51 (2002); Brummelkamp et al., Science 21 (2002); and Sui et al., Proc. Natl Acad. Sci. USA 99, 5515-5520 (2002). RNA interference (RNAi) is the process of sequence-specific post-transcriptional gene silencing in animals initiated by double-stranded (dsRNA) that is homologous in sequence to the silenced gene. siRNAs are generally RNA duplexes with each strand being 20-25 (such as 19-21) base pairs in length. In some embodiments, the checkpoint modulator is a short hairpin RNA (shRNA) that is complementary to a nucleic acid (e.g., a mRNA) of the checkpoint protein or a fragment thereof. An shRNA typically contains of a stem of 19-29 base pairs, a loop of at least 4 nucleotides (nt), and optionally a dinucleotide overhang at the 3' end. Expression of shRNA in a subject can be obtained by delivery of a vector (e.g., a plasmid or viral or bacterial vectors) encoding the shRNA. siRNAs and shRNAs may be designed using any method known in the art or commercially available (see, e.g., products available from Dharmacon and Life Technologies). An siRNA may also comprise one or more chemical modifications, such as a base modification and/or a bond modification to at least improve its stability and binding affinity to the target mRNA.

In some embodiments, the checkpoint modulator is an antisense oligonucleotide that is complementary to a nucleic acid (e.g., an mRNA) of the checkpoint protein. Antisense oligonucleotides are generally single-stranded nucleic acids (a DNA, RNA, or hybrid RNA-DNA molecule), which are complementary to a target nucleic acid sequence, such as a portion of the mRNA of the checkpoint protein. By binding to the target sequence, an RNA-RNA, a DNA-DNA, or RNA-DNA duplex is formed, thereby inhibiting the function or level of the target nucleic acid, such as by blocking the transcription, processing, poly(A) addition, replication, translation, or promoting modulatory mechanisms of the cells, such as promoting mRNA degradation. In some embodiments, an antisense oligonucleotide is 10 to 40, 12 to 35, or 15 to 35 bases in length, or any integer in between. An antisense oligonucleotide can comprise one or more modified bases, such as 2-Aminopurine, 2,6-Diaminopurine (2-Amino-dA), 5-Bromo dU, 5-Methyl dC, deoxyInosine, Locked Nucleic Acid (LNA), 5-Nitroindole, 2'-O-Methyl bases, Hydroxmethyl dC, 2' Fluoro bases. An antisense oligonucleotide can comprise one or more modified bonds, such as a phosphorothioate bond.

In some embodiments, the checkpoint modulator is a ribozyme that is complementary to a nucleic acid (e.g., an mRNA) of the checkpoint protein and cleaves the nucleic acid. Ribozymes are RNA or RNA-protein complexes that cleave nucleic acids in a site-specific fashion. Ribozymes have specific catalytic domains that possess endonuclease activity. The ribozymes of the present disclosure may be synthetic ribozymes, such as those described in U.S. Pat. No. 5,254,678. These synthetic ribozymes have separate hybridizing regions and catalytic regions; therefore, the hybridizing regions can be designed to recognize a target sequence, such as a sequence as described herein corresponding to a checkpoint protein.

siRNAs, shRNAs, ribozymes, and antisense oligonucleotides as described herein may be complementary to a nucleic acid (e.g., a mRNA) of a checkpoint protein, or a portion thereof. It is to be understood that complementarity includes 100% complementarity but does not necessarily exclude mismatches at one or more locations, resulting in, e.g., at least 80%, at least 90%, at least 95%, at least 98%, or at least 99% complementarity.

When applicable, the checkpoint modulator can be expressed from a vector, which may be used for delivering the checkpoint modulator into a subject who needs an anti-cancer therapy. A "vector", as used herein is any vehicle capable of facilitating the transfer of a checkpoint modulator (e.g., a shRNA, siRNA, ribozyme, antisense oligonucleotide, protein, peptide, or antibody) to a cell in the subject, such as a cell expressing the checkpoint protein. In general, vectors include, but are not limited to, plasmids, phagemids, viruses, and other vehicles derived from viral or bacterial sources that have been manipulated by the insertion or incorporation of a sequence encoding a checkpoint modulator. Viral vectors include, but are not limited to nucleic acid sequences from the following viruses: retrovirus; lentivirus; adenovirus; adeno-associated virus; SV40-type viruses; polyoma viruses; Epstein-Barr viruses; papilloma viruses; herpes virus; vaccinia virus; polio virus. One can readily employ other vectors not named but known to the art.

Viral vectors may be based on non-cytopathic eukaryotic viruses in which nonessential genes have been replaced with a sequence encoding a checkpoint modulator. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are known in the art.

Other viral vectors include adeno-viruses and adeno-associated viruses, which are double-stranded DNA viruses that have also been approved for human use in gene therapy. The adeno-associated virus can be engineered to be replication deficient and is capable of infecting a wide range of cell types and species.

Other vectors include plasmid vectors. Plasmid vectors have been extensively described in the art and are well known to those of skill in the art. See, e.g., Sambrook et al. Molecular Cloning: A Laboratory Manual. Cold Spring Harbor Laboratory Press; 4th edition (Jun. 15, 2012). Exemplary plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA, such as a sequence encoding an immune checkpoint modulator.

In some embodiments, a checkpoint modulator nucleic acid sequence can be under the control of a heterologous regulatory region, e.g., a heterologous promoter. The promoter can be, e.g., a ubiquitous promoter such as a CMV promoter, ActB promoter, or Ubiquitin B promoter. The promoter can also be a tissue-specific promoter or synthetic promoter. Promoters are well known in the art and commercially available (see, e.g., products available from Invivo-Gen).

In some embodiments, the checkpoint modulator can be a non-antibody peptide or protein. The peptide or protein may comprise an amino acid sequence that interferes with the checkpoint signaling, such as by competing with a natural ligand for the involved checkpoint protein. Proteins and peptides may be designed using any method known in the art, e.g., by screening libraries of proteins or peptides for binding to a checkpoint protein or inhibition of the checkpoint protein from binding to a ligand. In some examples, the non-antibody peptide or protein modulator can be a soluble receptor, for example, an Fc-fusion soluble receptor.

In some embodiments, a checkpoint modulator can be a fragment or variant of the checkpoint protein itself, e.g., a fragment that binds a cognate ligand thereof but does not transmit the corresponding signaling. A checkpoint modulator of this type can be a dominant negative modulator.

In some embodiments, the checkpoint modulator is a small molecule, such as a small organic molecule, which typically has a molecular weight less than 5,000 kDa. Suitable small molecules include those that bind to an immune checkpoint molecule, or a fragment thereof, and may be identified by methods such as screening large libraries of compounds (Beck-Sickinger & Weber (2001) Combinational Strategies in Biology and Chemistry (John Wiley & Sons, Chichester, Sussex); by structure-activity relationship by nuclear magnetic resonance (Shuker et al (1996) "Discovering high-affinity ligands for proteins: SAR by NMR. Science 274: 1531-1534); encoded self-assembling chemical libraries Melkko et al (2004) "Encoded self-assembling chemical libraries." Nature Biotechnol. 22: 568-574); DNA-templated chemistry (Gartner et al (2004) "DNA-tem plated organic synthesis and selection of a library of macrocycles. Science 305: 1601-1605); dynamic combinatorial chemistry (Ramstrom & Lehn (2002) "Drug discovery by dynamic combinatorial libraries." Nature Rev. Drug Discov. 1: 26-36); tethering (Arkin & Wells (2004) "Small-molecule modulators of protein-protein interactions: progressing towards the dream. Nature Rev. Drug Discov. 3: 301-317); and speed screen (Muckenschnabel et al (2004) "SpeedScreen: label-free liquid chromatography-mass spectrometry-based high-throughput screening for the discovery of orphan protein ligands." Anal. Biochem. 324: 241-249).

Typically, small molecules will have a dissociation constant for an immune checkpoint protein in the nanomolar range.

Pharmaceutical Compositions Containing Checkpoint Modulators

Any of the immune checkpoint modulators, e.g., antibodies, the encoding nucleic acids or nucleic acid sets, vectors comprising such, siRNAs, antisense RNAs, and vectors carrying such, and small molecule modulators, can be mixed with a pharmaceutically acceptable carrier (excipient) to form a pharmaceutical composition for use in treating a target disease (e.g., cancer). "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some examples, the pharmaceutical composition described herein comprises liposomes containing the antibodies (or the encoding nucleic acids) which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%.

It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

(b) Fermented Compositions of Legume Plants

Fermentation is a metabolic process, in which microorganisms such as yeast and bacteria convert carbohydrates to acids (e.g., organic acids such as lactic acids), alcohols (e.g., ethanol) and/or other metabolites under anaerobic conditions. The fermented composition for use in the combined anti-cancer therapy as described herein is a fermentation product of one or more legume plants by one or more suitable microorganisms, for example a population of symbiotic microbiota. Such a fermented composition may comprise multiple metabolites derived from fermenting a suitable starting material, for example, a legume plant, a portion thereof (e.g., leave, fruit, seed, etc.), or an extract thereof, by one or more suitable microorganisms, via, e.g., a conventional fermentation process. Suitable microorganisms include, but are not limited to, yeast and *lactobacillus*. See, e.g., US20060251748, the relevant disclosures of which are incorporated by reference herein for the purposes or subject matter referenced herein. In some embodiments, the fermented composition described herein may comprise one or more of metabolites such as lactic acid, acetic acid, and 3-aminoisobutyric acid. For example, the fermented composition may comprise about 5-20% by weight lactic acid (e.g., 5-10%, 10-20%, 5-15%, or 15-20% by weight). Alternative or in addition, the fermented composition may comprise less than 5% by weight acetic acid, 3-aminoisobutyric acid, or both (e.g., 1-5%, 0.5-5%, 1-3%, 0.5-3%, or 3-5% by weight).

Exemplary legume plants include, but are not limited to, beans, peas, alfalfa, red clover, fava, vetch, and cowpeas. In some embodiments, the fermented composition for use in the combined anti-cancer therapy disclosed herein is a fermented soybean composition, which comprises multiple metabolites that are generated via fermentation of soybeans or an extract thereof (e.g., an aqueous extract) by one or more suitable microorganisms such as yeast and *lactobacillus*. As well known in the art, such metabolites may be generated via alternative processes, which are also within the scope of the present disclosure.

Any of the fermented compositions described herein, such as fermented soybean compositions, may be prepared by fermenting a legume plant, a portion thereof, or an extract thereof by one or more suitable microorganisms such as those described herein under suitable conditions allowing for fermentation of the components of the legume plant to produce metabolites thereof. For example, a fermented composition may be prepared by culturing the one or more suitable microorganisms in a medium comprising an aqueous extract of a legume plant of a portion thereof under suitable conditions (e.g., a suitable temperature of, for example, 20-45° C. (e.g., 20-25° C., 20-30° C., 25-30° C., 25 to 35° C., 30-45° C., or 30-40° C.) for a suitable period of time (e.g., 2-10 days such as 2-5 days, 4-8 days, and 5-10 days). The one or more microorganisms for use in preparing the fermented composition can be symbiotic, which refers to diverse organisms that live together and benefit each other. The supernatant of the culture can then be collected, filtered to remove solid components, and sterilized. When necessary, the supernatant may be concentrated by a conventional method (e.g., dialysis) to produce a concentrated fermented composition solution.

In one example, the fermented composition is a fermented soybean composition, which can be prepared by obtaining an aqueous extract of soybeans via a conventional method, fermenting the aqueous extract with a mixture of at least one *Lactobacillus* and at least one *Saccharomyces* under suitable conditions for a suitable period to form a fermented liquid, collecting, filtering, and sterilizing the fermented liquid, and removing water from the sterilized and fermented liquid to form a concentrated fermented soybean composition.

In some examples, the fermented composition is in liquid form. In other examples, the fermented composition may be in dry form, for example, powder, which can be prepared by routine practice (e.g., spray drying or freeze drying).

Methods for preparing fermented compositions are also described in, e.g., U.S. Pat. Nos. 6,685,973, 6,855,350, 6,733,801, and US20120058104, the relevant disclosures of each of which are incorporated by reference herein for the purposes or subject matter referenced herein.

Any of the fermented compositions described herein may be formulated as pharmaceutical composition following the descriptions provided herein.

In other embodiments, the fermented compositions may be formulated as healthy food products, nutraceutical products or medical food products, which can be any kinds of liquid and solid/semi-solid materials to improve immunity in cancer patients, including those who have been undergone or is being treated with an immune checkpoint modulator. The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

The health food product, nutraceutical products, and/or medical food products described herein, containing any of the fermented compositions such as a fermented soybean composition, may comprise one or more edible carriers, which confer one or more of the benefits to the fermented composition as described herein. Examples of edible carriers include starch, cyclodextrin, maltodextrin, methylcellulose, carbonmethoxy cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art.

In some examples, the fermented composition can be a nutraceutical composition, which refers to compositions containing components from food sources and conferring extra health benefits in addition to the basic nutritional value found in foods. A nutraceutical composition as described herein comprises the fermented composition and additional ingredients and supplements that promote good health and/or enhance stability and bioactivity of the fermented composition.

The actions of nutraceutical compositions may be fast or/and short-term or may help achieve long-term health objectives as those described herein, e.g., improving immunity in a subject against cancer and enhancing the anticancer effect of an immune checkpoint modulator. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

In some embodiments, the fermented composition described herein, such as a fermented soybean composition, may be formulated as medical food products. A medical food product is a food product formulated to be consumed or administered enterally. Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from cancer). In some examples, a medical food composition described herein is not one of those that would be simply recommended by a physician as part of an overall diet to manage the symptoms or reduce the risk of a disease or condition.

Any of the medical food compositions described herein, comprising the fermented composition as described herein, can be in the form of a liquid solution; powder, bar, wafer, a suspension in an appropriate liquid or in a suitable emulsion, as detailed below. The at least one carrier, which can be either naturally-occurring or synthetic (non-naturally occurring), would confer one or more benefits to the fermented composition, for example, stability, bioavailability, and/or bioactivity. Any of the carriers described herein may be used for making the medical food composition. In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

The fermented compositions disclosed herein can be in the form of a solution. For example, the fermented composition can be provided in a medium, such as a buffer, a solvent, a diluent, an inert carrier, an oil, or a creme. In some examples, the fermented composition is present in an aqueous solution that optionally contains a non-aqueous co-solvent, such as an alcohol. The fermented composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The fermented compositions may be formulated for a suitable administration route, for example, oral administration. For oral administration, the composition can take the form of, for example, tablets or capsules, prepared by conventional means with acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

In some examples, the fermented composition can be in a liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates, benzoate or sorbate).

In some embodiments, the fermented composition and the immune checkpoint modulator as described herein may be formulated in one composition.

II. Kits for Treating Cancer

The present disclosure also provides kits for use in treating cancer with any of the immune checkpoint modulators described herein and any of the fermented composition (e.g., fermented soybean composition) also described herein. Such kits can include one or more containers comprising an immune checkpoint modulator and a fermented composition. For example, the kit may include an anti-PD1 antibody or its encoding nucleic acid, and a fermented soybean composition.

In some embodiments, the kit can comprise instructions for use in accordance with any of the methods described herein. The included instructions can comprise, for example, a description of administration of an immune checkpoint modulator and a fermented composition to treat, delay the onset, or alleviate a proliferative disease such as cancer (e.g., colon cancer or lung cancer) according to any of the methods described herein. The kit may further comprise a description of selecting an individual suitable for treatment based on identifying whether that individual has the disease. In still other embodiments, the instructions comprise a description of administering one or more agents of the disclosure to an individual at risk of the disease.

The instructions relating to the use of an immune checkpoint modulator such as an anti-checkpoint antibody in combination with a fermented composition (e.g., a fermented soybean composition) generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert may indicate that the composition is used for treating, alleviating and/or delaying the onset of cancer. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container. In some embodiments, the invention provides articles of manufacture comprising contents of the kits described above.

Combined Therapy

Provided herein are combined cancer therapies using a combination of an immune checkpoint modulator and a fermented composition as described herein. The term combination therapy, as used herein, embraces administration of these agents (e.g., an immune checkpoint modulator and a fermented composition) in a sequential manner, that is, wherein each therapeutic agent is administered at a different time, as well as administration of these therapeutic agents, or at least two of the agents, in a substantially simultaneous manner. Sequential or substantially simultaneous administration of each agent can be affected by any appropriate route including, but not limited to, oral routes, intravenous routes, intramuscular, subcutaneous routes, and direct absorption through mucous membrane tissues. The agents can be administered by the same route or by different routes. For example, a first agent (e.g., a fermented composition) can be administered orally, and a second agent (e.g., an anti-checkpoint antibody such as an anti-PD1 antibody) can be administered intravenously. Further, an agent of the combination selected may be administered by intravenous injection while the other agents of the combination may be administered orally. Alternatively, for example, two or more of the agents may be administered by intravenous or subcutaneous injection.

As used herein, the term "sequential" means, unless otherwise specified, characterized by a regular sequence or order, e.g., if a dosage regimen includes the administration of an immune checkpoint modulator such as an antibody and a fermented composition, a sequential dosage regimen could include administration of the immune checkpoint modulator before, simultaneously, substantially simultaneously, or after administration of the fermented composition, but both agents will be administered in a regular sequence or order. The term "separate" means, unless otherwise specified, to keep apart one from the other. The term "simultaneously" means, unless otherwise specified, happening or done at the same time, i.e., the agents of the present disclosure are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two compounds separately). As used herein, concurrent administration and substantially simultaneous administration are used interchangeably. Sequential administration refers to temporally separated administration of the agents described herein.

Combination therapy can also embrace the administration of the agents described herein (e.g., an immune checkpoint modulator and a fermented composition) in further combination with other biologically active ingredients (e.g., a different antineoplastic agent) and non-drug therapies (e.g., surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It should be appreciated that any combination of an immune checkpoint modulator, and a fermented composition as described herein may be used in any sequence for treating cancer. The combinations described herein may be selected on the basis of a number of factors, which include, but are not limited to, the effectiveness of inhibiting or preventing cancer progression, the effectiveness for mitigating the side effects of another agent of the combination, or the effectiveness of mitigating cancer related symptoms. For example, a combined therapy described herein may reduce any of the side effects associated with each individual members of the combination. Some examples are provided in the below tables. For example, the fermented composition may be used during the course of a treatment involving an immune checkpoint modulator (e.g., an anti-PD1 antibody) on a daily basis.

Any of the combinations of an immune checkpoint modulator and a fermented composition, as described herein, are useful for treating cancer. The term "cancer" as used herein refers to a medical condition mediated by neoplastic or malignant cell group, proliferation, or metastasis, including solid cancers and non-solid cancers. Examples of cancer include but are not limited to, lung cancer, kidney cancer, gastric cancer, breast cancer, brain cancer, prostate cancer, hepatocellular cancer, pancreatic cancer, cervical cancer, ovarian cancer, liver cancer, bladder cancer, cancer of the urinary tract, thyroid cancer, melanoma, head and neck cancer, colon cancer, leukemia, lymphomas, skin cancer, stomach cancer, esophageal cancer, myelomas, rectal cancer, bone cancer, uterine cancer, prostate cancer, and hematological malignancy.

To practice the method disclosed herein, an effective amount of the anti-cancer agent combination as described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the immune checkpoint modulators as described herein (e.g., antibodies) and/or the fermented composition can be aerosolized using a fluorocarbon formulation and a metered dose inhaler, or inhaled as a lyophilized and milled powder.

The terms "subject," "individual," and "patient" are used interchangeably herein and refer to a mammal being assessed for treatment and/or being treated. Subjects may be human, but also include other mammals, particularly those mammals useful as laboratory models for human disease, e.g. mouse, rat, rabbit, dog, etc.

A human subject who needs the treatment may be a human patient having, at risk for, or suspected of having a target disease/disorder, such as a proliferative disease (e.g., cancer). A subject having a target disease or disorder can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors for that disease/disorder. The methods and compositions described herein may be used to treat any proliferative disease or disorder. In some embodiments, the proliferative disease is cancer. In some embodiments the cancer is characterized by a solid tumor.

As used herein, "an effective amount" refers to the amount of each active agent (e.g., an immune checkpoint modulator such as an anti-PD1 antibody or a fermented composition) required to confer therapeutic effect on the subject, either alone or in combination with one or more other active agents. In some embodiments, the therapeutic effect is suppressing cancer cell growth and/or reducing tumor burden. In some embodiments, the amount of the fermented composition is effective in enhancing the anti-cancer effect of the immune checkpoint modulator. In other embodiments, the amount of the fermented composition is effective in enhancing immunity of the subject against cancer cells. In some embodiments, the therapeutic effect is the prevention or inhibition of tumor growth. In some embodiments, the therapeutic effect is a decrease in a side effect associated with one or more agents/drugs. For example, a side effect that may result from inhibiting the PD-1 pathway (e.g., fatigue, peripheral oedema, chills, pyrexia, diarrhoea, nausea, abdominal pain, cough, dyspnoea, rash, pruritus, vitiligo, arthralgia, myalgia, back pain, headache, dizziness, and/or increased aspartate aminotransferase (AST)) may be reduced by co-treatment with an modulator of another agent (e.g., an immune checkpoint modulator and a fermented composition as described herein).

Determination of whether an amount of the modulator combination achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an immune checkpoint modulator such as an antibody as described herein may be determined empirically in individuals who have been given one or more administration(s) of the modulator. Individuals are given incremental dosages of the modulator. To assess efficacy of the antagonist, an indicator of the disease/disorder can be followed.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the antagonist, and the discretion of the attending physician. Typically the clinician will administer an antibody, until a dosage is reached that achieves the desired result. In some embodiments, the desired result is a decrease in thrombosis. Methods of determining whether a dosage resulted in the desired result would be evident to one of skill in the art. Administration of an immune checkpoint modulator and/or the fermented composition can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the combination of the immune checkpoint modulator and the fermented composition described herein are administered to a subject in need of the treatment at an amount sufficient to inhibit the activity of one or more target signaling pathway by at least 20% (e.g., 30%, 40%, 50%, 60%, 70%, 80%, 90% or greater) in vivo. In other embodiments, the combination is administered in an amount effective in reducing the activity level of one or more target antigens by at least 20% (e.g., 30%, 40%, 50%, 60%, 70%, 80%, 90% or greater).

In some embodiments, a fermented composition as described herein is given to a subject (e.g., a human cancer patient) who has been undergone or is under an anti-cancer treatment that involves the use of an immune checkpoint modulator (e.g., inhibitor) as described herein.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical compositions are administered intraocularlly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

Treatment efficacy for a target disease/disorder can be assessed by methods well-known in the art.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The specific embodiments provided herein are, therefore, to be construed as merely illustrative, and not limitative of the remainder of the disclosure in any way whatsoever. All publications cited herein are incorporated by reference for the purposes or subject matter referenced herein.

Example 1: Treating Colon Cancer with an Anti-PD1 Antibody and Composition X Via Oral Administration Composition X is a fermented soybean composition prepared as follows. An aqueous extract of soybean was prepared by conventional methods. A mixture of *Lactobacillus* and yeast were cultured in a medium containing the aqueous soybean extract under conditions that allow for fermentation of the soybean extract by the microorganisms. The fermented liquid were collected, filtered to remove solid materials, and sterilized. The liquid solution thus prepared was concentrated to produce Composition X (in liquid form). Each milligram of Composition X contains the fermented broth of about 2.7 g soybean.

The effectiveness of the combined therapy of Composition X and anti-PD1 antibody on colon cancer was investigated in a colon cancer mouse model. Briefly, Balb/c mice were injected subcutaneously with $2 \times 10^5$ colon cancer CT26 cells on Day 0. The mice were injected intraperitoneally with an anti-PD1 antibody at Day 6 at 10 mg/kg when the tumors derived from the grafted colon cancer cells grew to a volume of about 60-70 $mm^3$. The injection of the anti-PD1 antibody was repeated at the same dose at Days 8, 10, and 12. The mice were sacrificed at day 17 for analysis. During Day 0 to Day 15, some of the mice were fed with diluted Composition X (1%, 5%, or 15%) daily and others were fed with a vehicle control. A schematic illustration of this exemplary experimental design is provided in FIG. 1A.

Alternatively, Balb/c mice were fed with Composition X on a daily basis for two weeks (14 days; starting on Day-14). The mice were then injected subcutaneously with $2 \times 10^5$ colon cancer CT26 cells (on Day 0). Five days after the cancer cell transplantation (Day 5), the mice were treated with 10 mg/kg anti-PD1 via intraperitoneal injection, which is repeated on Days 7, 9, and 11. The mice were sacrificed on Day 15 for analysis.

Figure 1B:
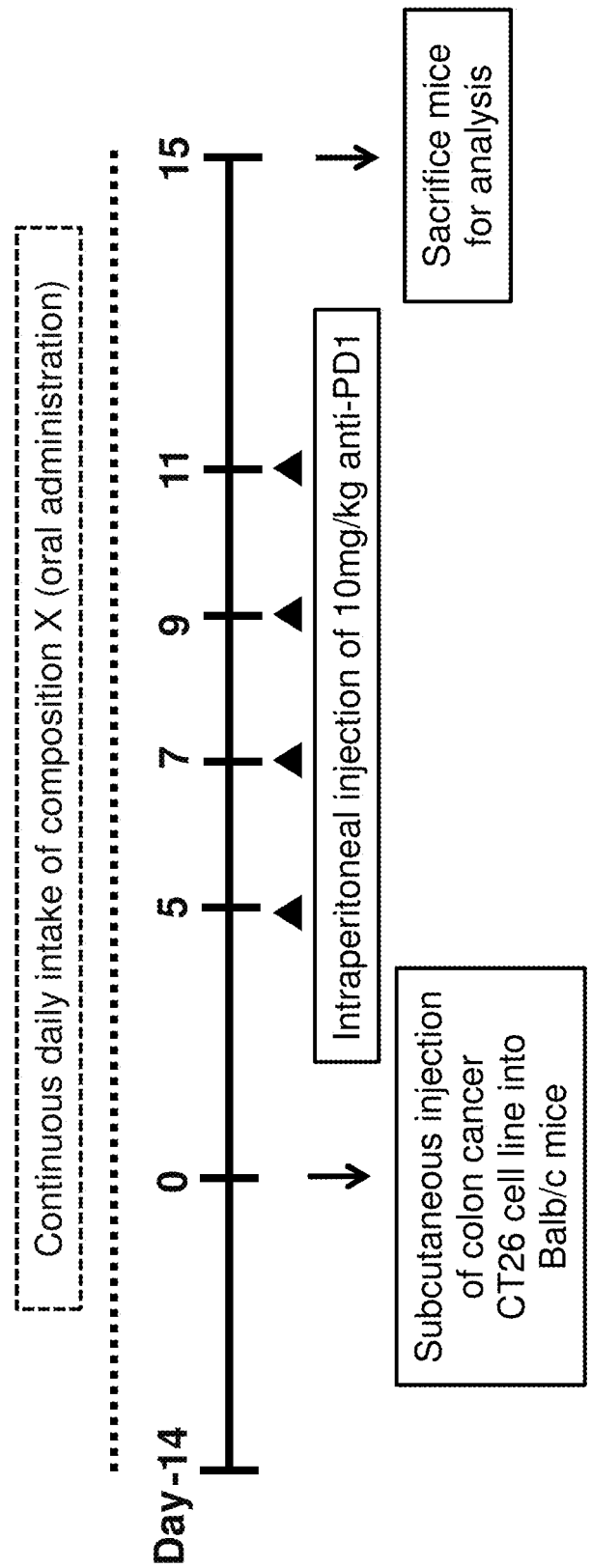
FIG. 1B is a schematic illustration of an experimental design for studying the effect of a combination of an anti-PD1 antibody and a fermented composition (Composition X) via oral administration in a colon cancer mouse model. The mice were treated with the fermented composition prior to the transplantation of colon cancer CT26 cells.
Figure 2A:
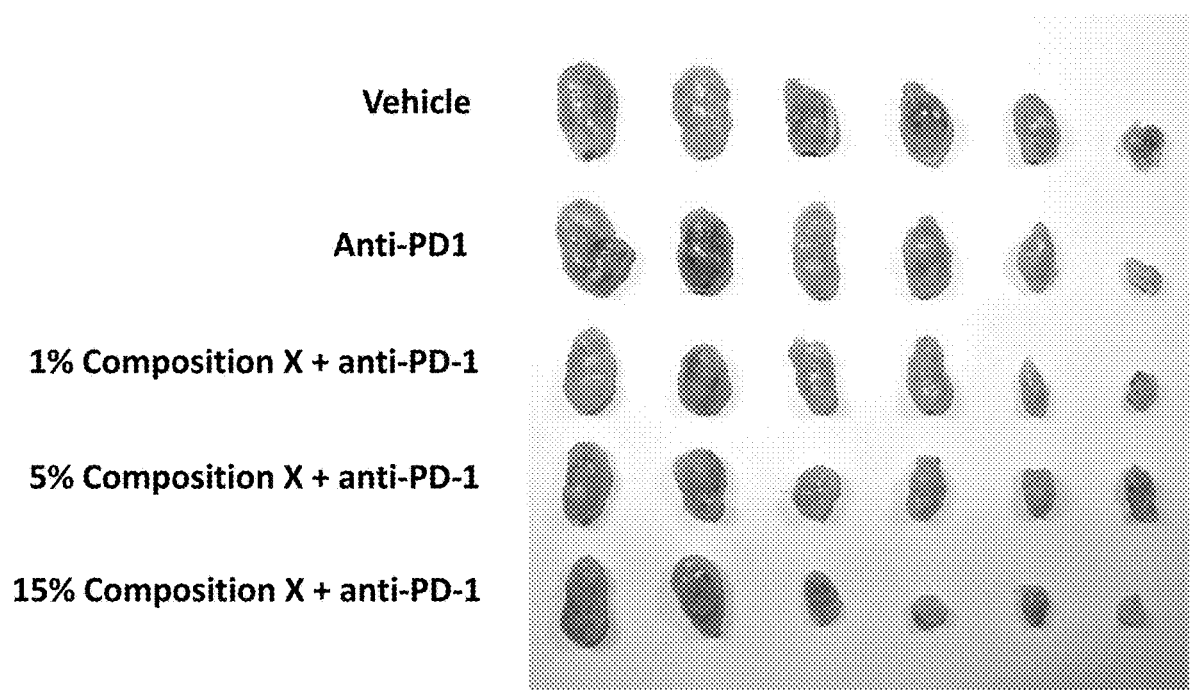
FIG. 2A is a photo showing sizes of tumors formed by subcutaneous injection of colon cancer CT26 cells in mice treated with vehicle control, an anti-PD1 antibody, or combinations of the anti-PD1 antibody and a fermented composition as various doses. The mice were concurrently transplanted with colon cancer CT26 cells and treated with of the fermented composition. No significant difference in body weight was observed among the groups.
Figure 2B:
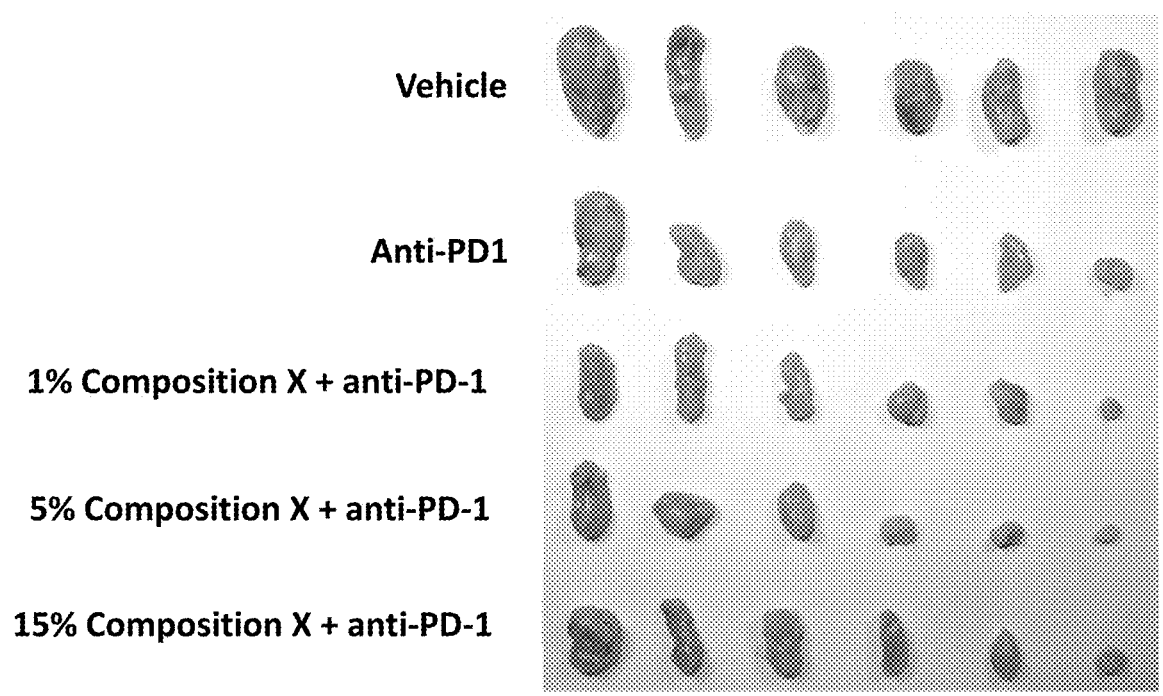
FIG. 2B is a photo showing sizes of tumors formed by subcutaneous injection of colon cancer CT26 cells in mice treated with vehicle control, an anti-PD1 antibody, or combinations of the anti-PD1 antibody and a fermented composition as various doses. The mice were treated with the fermented composition prior to the transplantation of colon cancer CT26 cells. No significant difference in body weight was observed among the groups.
Figure 3A:
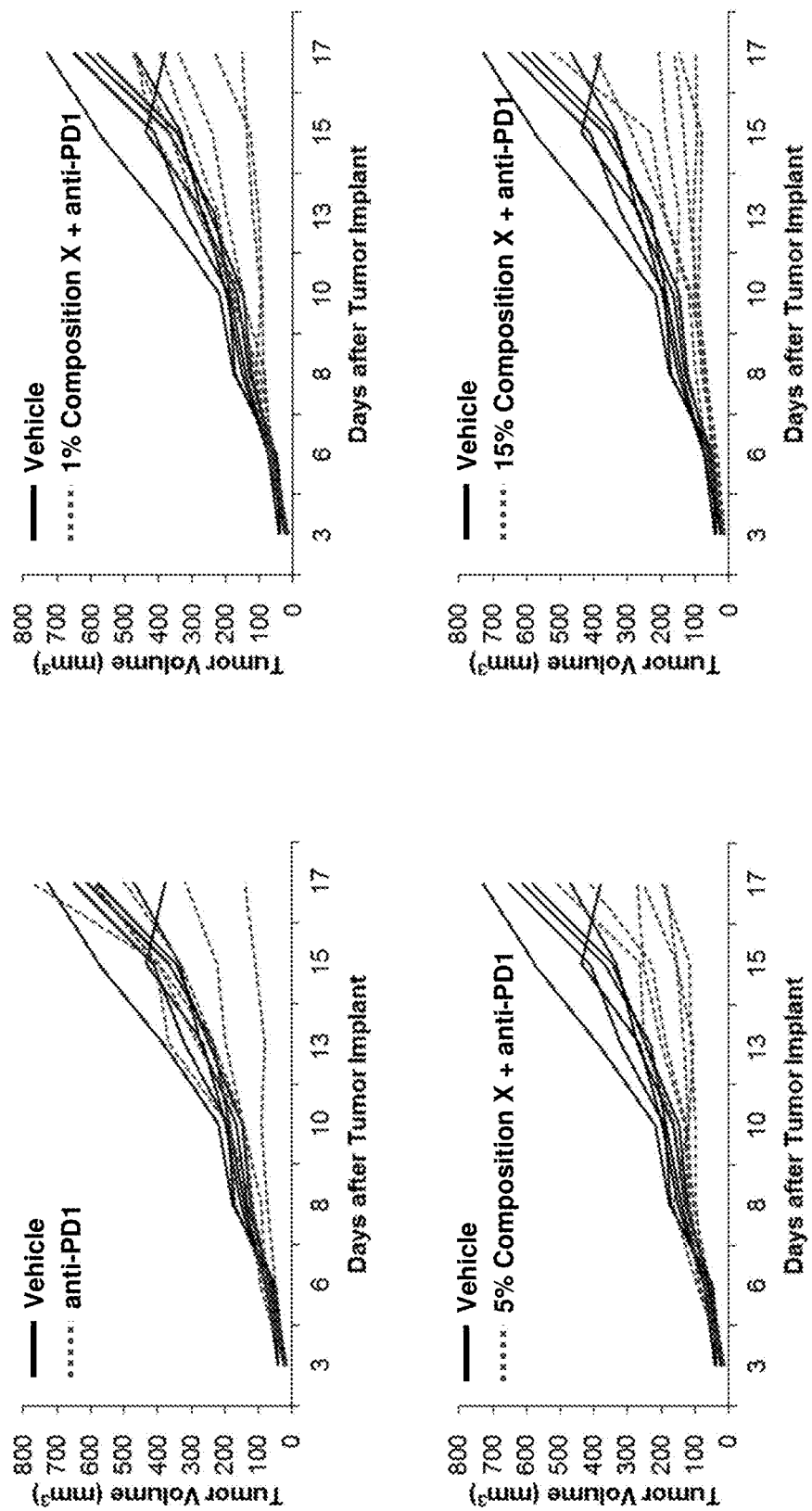
FIG. 3A includes charts showing the inhibitory effects of the anti-PD1/Composition X combination on tumor growth observed in a colon cancer mouse model. The mice were concurrently transplanted with colon cancer CT26 cells and treated with of the fermented composition.
Figure 3B:
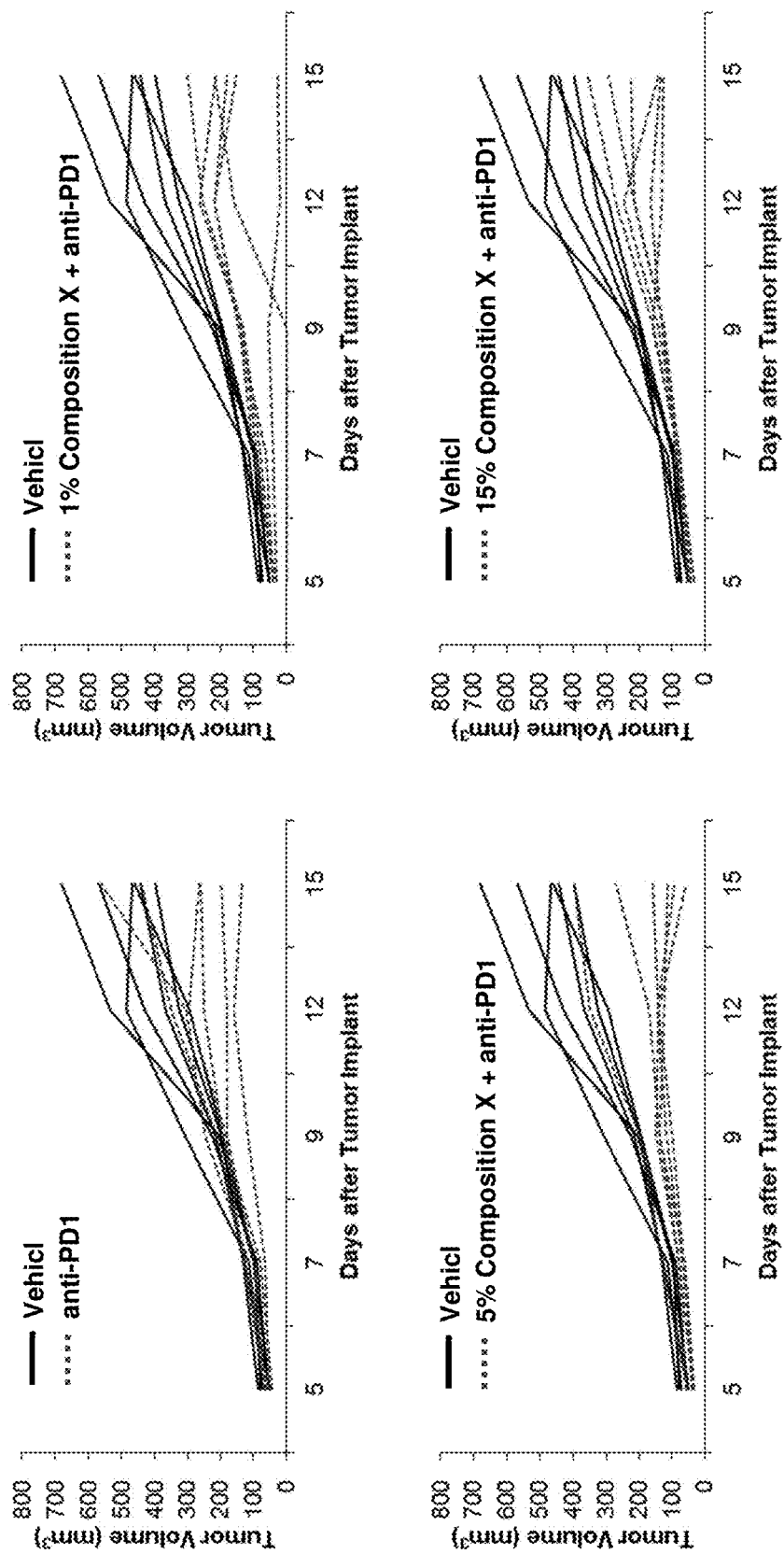
FIG. 3B includes charts showing the inhibitory effects of the anti-PD1/Composition X combination on tumor growth observed in a colon cancer mouse model. The mice were treated with the fermented composition prior to the transplantation of colon cancer CT26 cells.

As shown in Tables 1 and 2 below and FIGS. 2 and 3, Composition X significantly enhanced the efficacy of the anti-PD1 antibody in inhibiting tumor growth in a dose-dependent manner as demonstrated in the colon cancer mouse model used in this example. Table 1, FIG. 2A, and FIG. 3A show results obtained from a study following the experimental design depicted in FIG. 1A. Table 2, FIG. 2B, and FIG. 3B show results obtained from a study following the experimental design depicted in FIG. 1B.

TABLE 1

Effect of Composition X and anti-PD1 Antibody on Tumor Growth in Colon Cancer Mouse Model

| Group (n = 6) | Average Tumor Volume (mm³) | Tumor Growth Inhibition (%) |
|---|---|---|
| Vehicle | 570.4 | — |
| Anti-PD1 | 485.8 | 14.8 |
| 1% Composition X + anti-PD1 | 344.7 | 39.6 |
| 5% Composition X + anti-PD1 | 304.8 | 46.6 |
| 15% Composition X + anti-PD1 | 256.5 | 55.0 |

TABLE 2

Effect of Composition X and anti-PD1 Antibody on Tumor Growth in Colon Cancer Mouse Model

| Group | Average Tumor Volume (mm³) | Tumorinhibition rate (%) |
|---|---|---|
| Vehicle | 502.8 | — |
| anti-PD1 mAb | 308.6 | 38.6 |
| 1% Composition X + anti-PD1 mAb | 182.2 | 63.8 |
| 5% Composition X + anti-PD1 mAb | 181.4 | 63.9 |
| 15% Composition X + anti-PD1 mAb | 213.3 | 57.6 |

On Day 15, the mice were sacrificed and splenocytes from each mouse were stained with fluorescence-labeled CD4, CD8, CD62L and CD44 antibodies for flow cytometry analysis. Three-color flow cytometry was performed to identify naïve T cells (defined as CD62L+CD44low) and effector memory T cells (defined as CD62L-CD44high).

Figure 4:
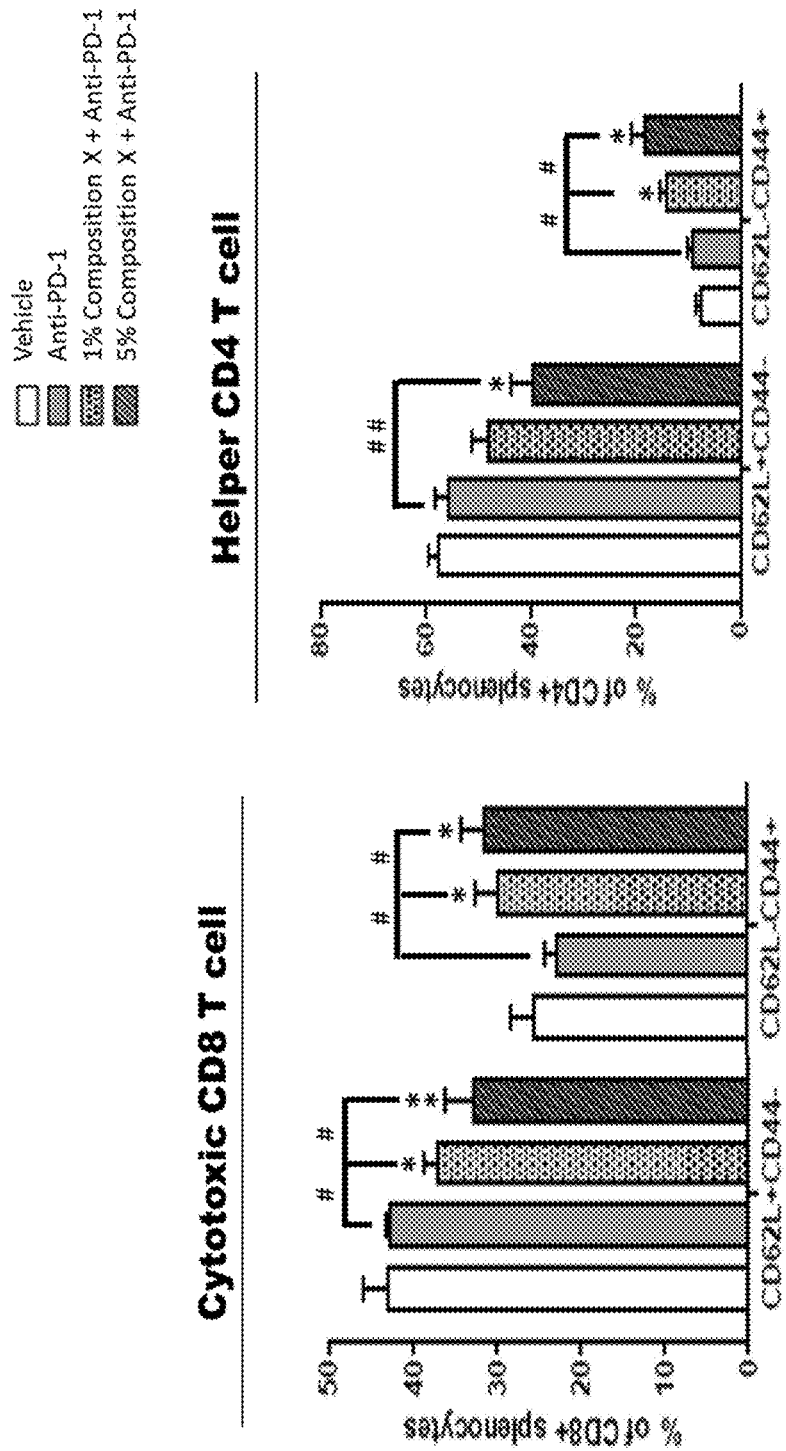
FIG. 4 includes charts showing the effect of Composition X-anti-PD1 combinations on splenic T cell profiling observed in a colon cancer mouse model. *p<0.05; p<0.01; and *p<0.001. P-values were obtained by comparison of each intervention group and the control group (vehicle treated). #p<0.05; ##p<0.01; ###p<0.001. P-values were obtained by comparison of each intervention group and the anti-PD1 antibody-treated group.

As shown in FIG. 4, the percentages of effector memory T cells in both splenic CD8+ and CD4+ cells were significantly increased as a result of the combined treatment of anti-PD1 and Composition X, while naïve T cells decreased as compared with the control.

Example 2: Treating Lung Cancer with an Anti-PD1 Antibody and Composition X Via Oral Administration Composition X was prepared as described in Example 1 above. The effectiveness of the combined therapy of Composition X and anti-PD1 antibody on lung cancer was investigated in a lung cancer mouse model as follows.

Figure 5:
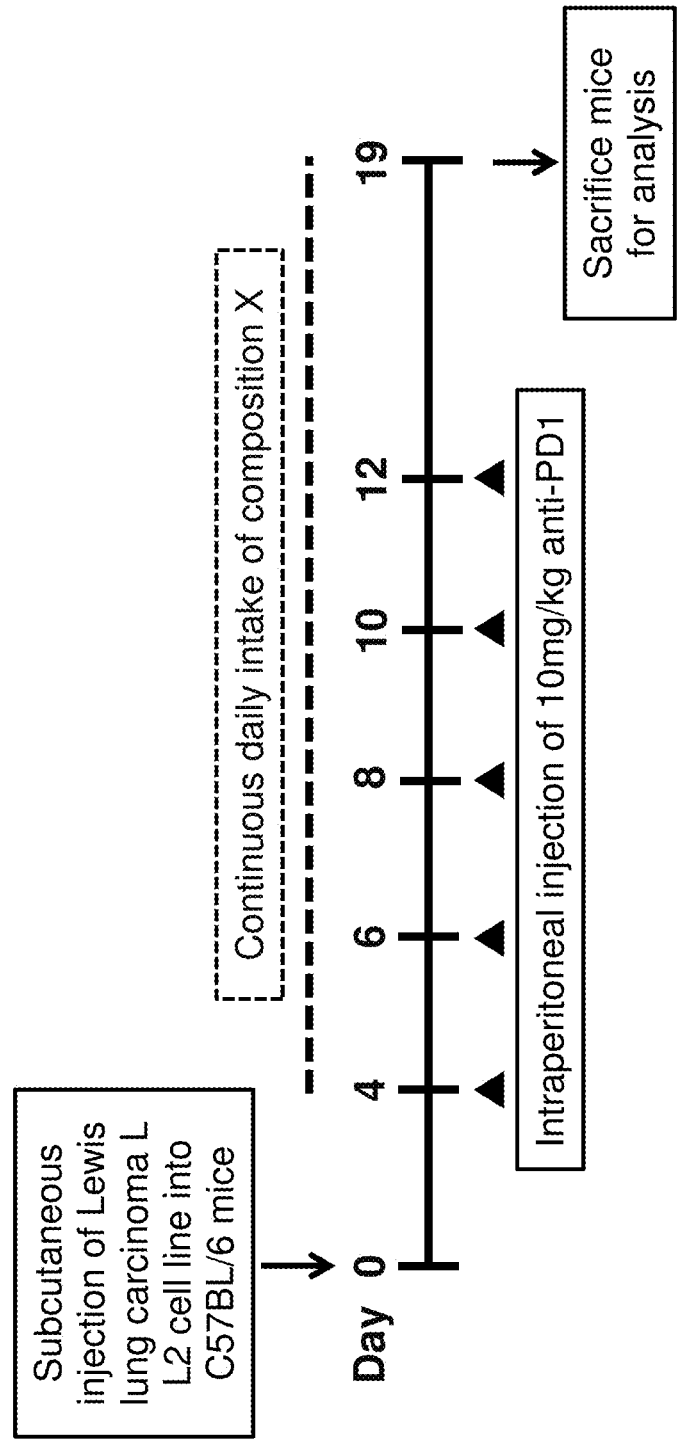
FIG. 5 is a schematic illustration of an exemplary experimental design for studying the effect of Composition X-anti-PD1 combinations in a lung cancer mouse model.

C57BL/6 mice were injected with $5 \times 10^6$ lung cancer LL2 cells on Day 0. Starting from Day 4, some of the mice were fed with diluted Composition X (7.5%, 15% or 22.5% composition) once every day, and the others were treated with a vehicle control. Starting at Day 4, when the tumor grew to a volume around 60 mm³, the mice were injected intraperitoneally with 10 mg/kg an anti-PD1 monoclonal antibody once every other day (on Days 4, 6, 8, 10, and 12). The Mice were sacrificed on Day 19 for analysis. A schematic illustration of this exemplary experimental design is provided in FIG. 5.

Figure 6:
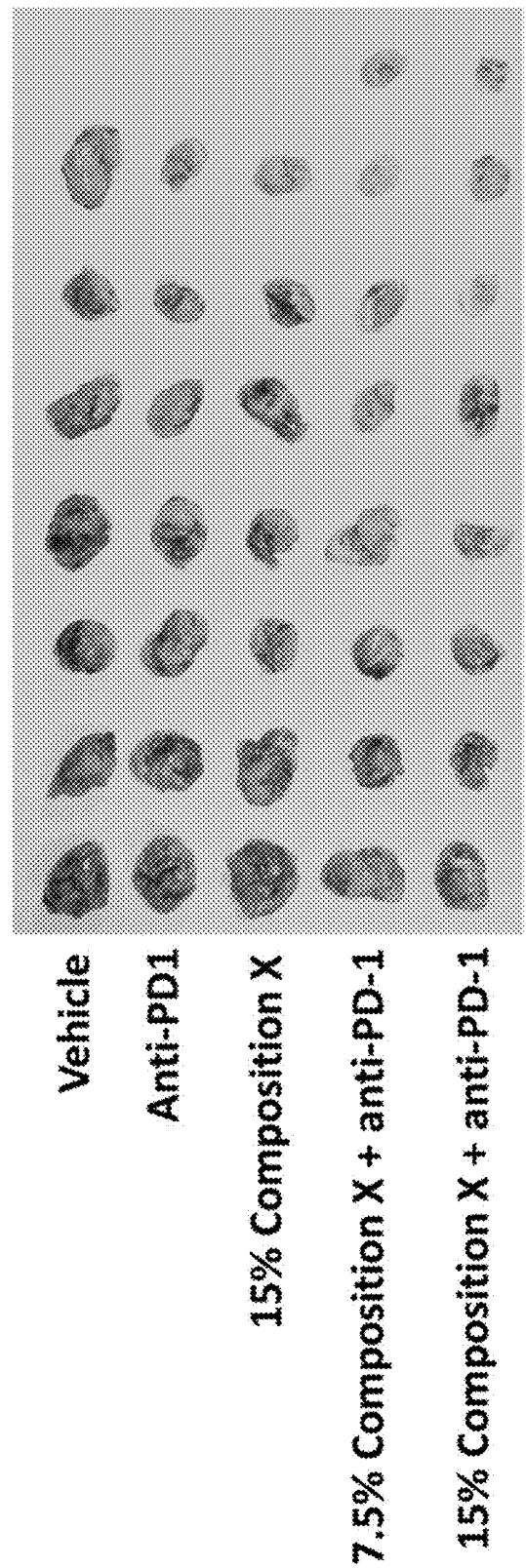
FIG. 6 is a photo showing sizes of tumors formed by subcutaneous injection of lung carcinoma LL2 cells in mice treated with vehicle control, an anti-PD1 antibody, or combinations of the anti-PD1 antibody and a fermented composition as various doses. No significant difference in body weight was observed among the groups.
Figure 7:
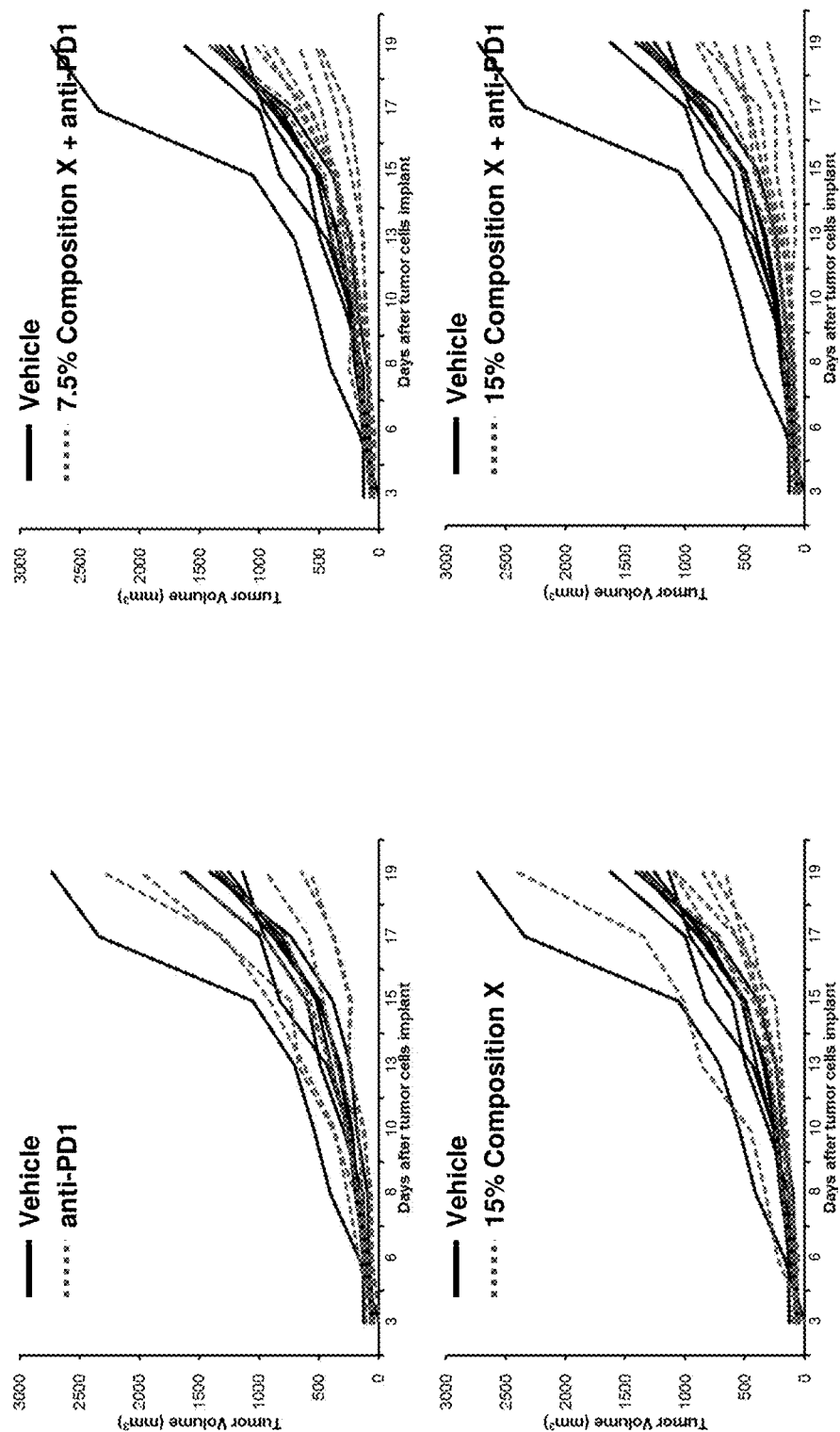
FIG. 7 includes charts showing the inhibitory effects of the anti-PD1/Composition X combination on tumor growth observed in a lung cancer mouse model.

As shown in Table 3 below and FIGS. 6 and 7, Composition X significantly enhances the efficacy of anti-PD1 in inhibiting tumor growth in a dose-dependent manner as observed in this lung cancer mouse model. Composition X acted synergistically with the anti-PD1 antibody in suppressing tumor growth.

TABLE 3

Effect of Composition X and anti-PD1 Antibody on Tumor Growth in Lung Cancer Mouse Model

| Group (n = 7 or 8) | Average Tumor Volume (mm³) | Tumor Growth Inhibition (%) |
|---|---|---|
| Vehicle | 1551.9 | — |
| Anti-PD1 | 1354.4 | 12.7 |
| 15% Composition X | 1179.5 | 24.0 |
| 7.5% Composition X + anti-PD1 | 921.0 | 40.7 |
| 15% Composition X + anti-PD1 | 755.3 | 51.3 |

Figure 8:
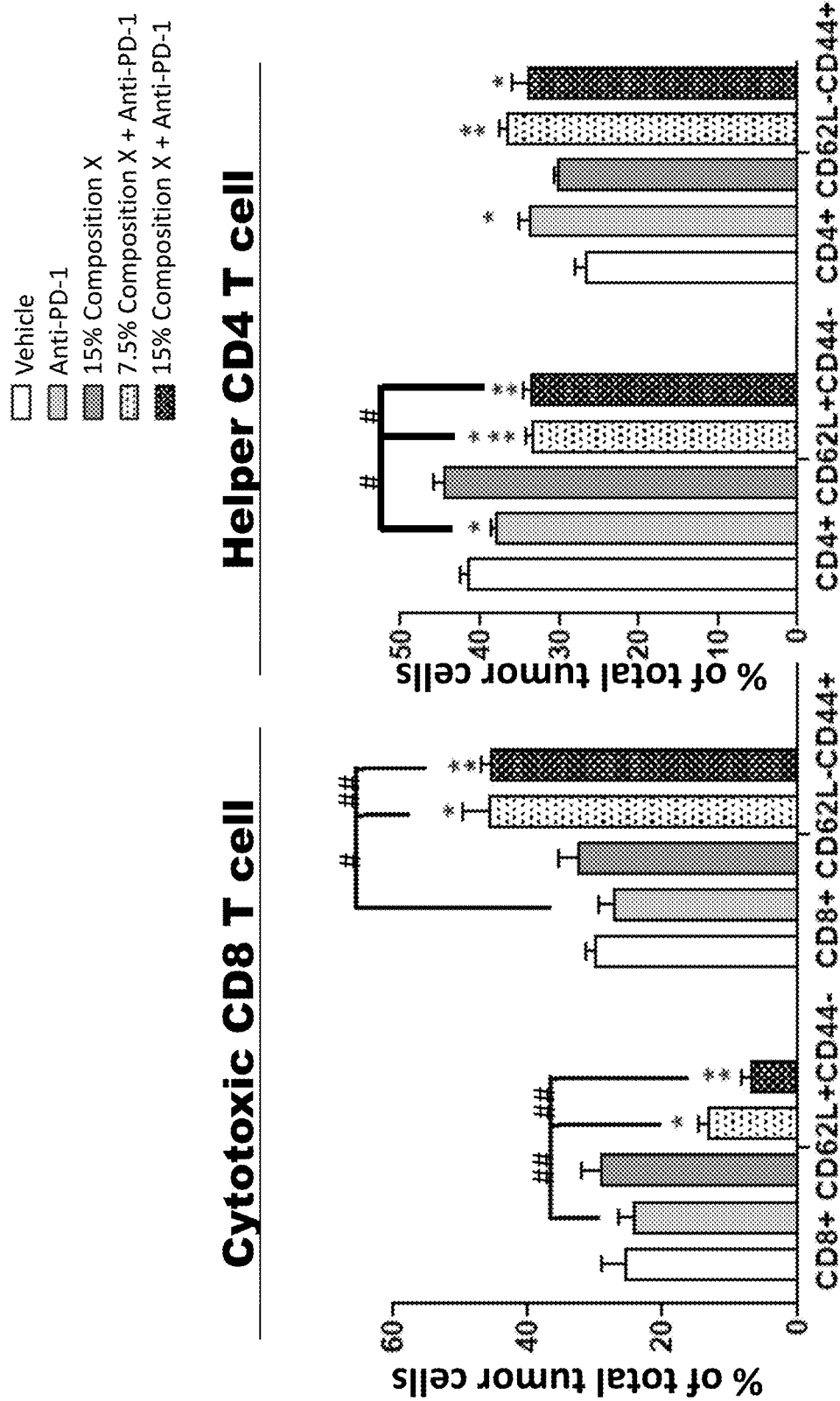
FIG. 8 includes charts showing the effect of Composition X-anti-PD1 combinations on tumor-infiltrating T cell profiling observed in a lung cancer mouse model. *p<0.05; p<0.01; and *p<0.001. P-values were obtained by comparison of each intervention group and the control group (vehicle treated). #p<0.05; ##p<0.01; ###p<0.001. P-values were obtained by comparison of each intervention group and the anti-PD1 antibody-treated group.

Both CD4+ and CD8+ T cells infiltrated into tumor tissues were analyzed by flow cytometry as described herein. It was observed that, in both tumor-infiltrating CD4+ and CD8+ T cells, the percentages of effector memory T cells significantly increased as a result of the combined treatment, while naïve T cells decreased as compared with the vehicle control. FIG. 8.

Figure 9:
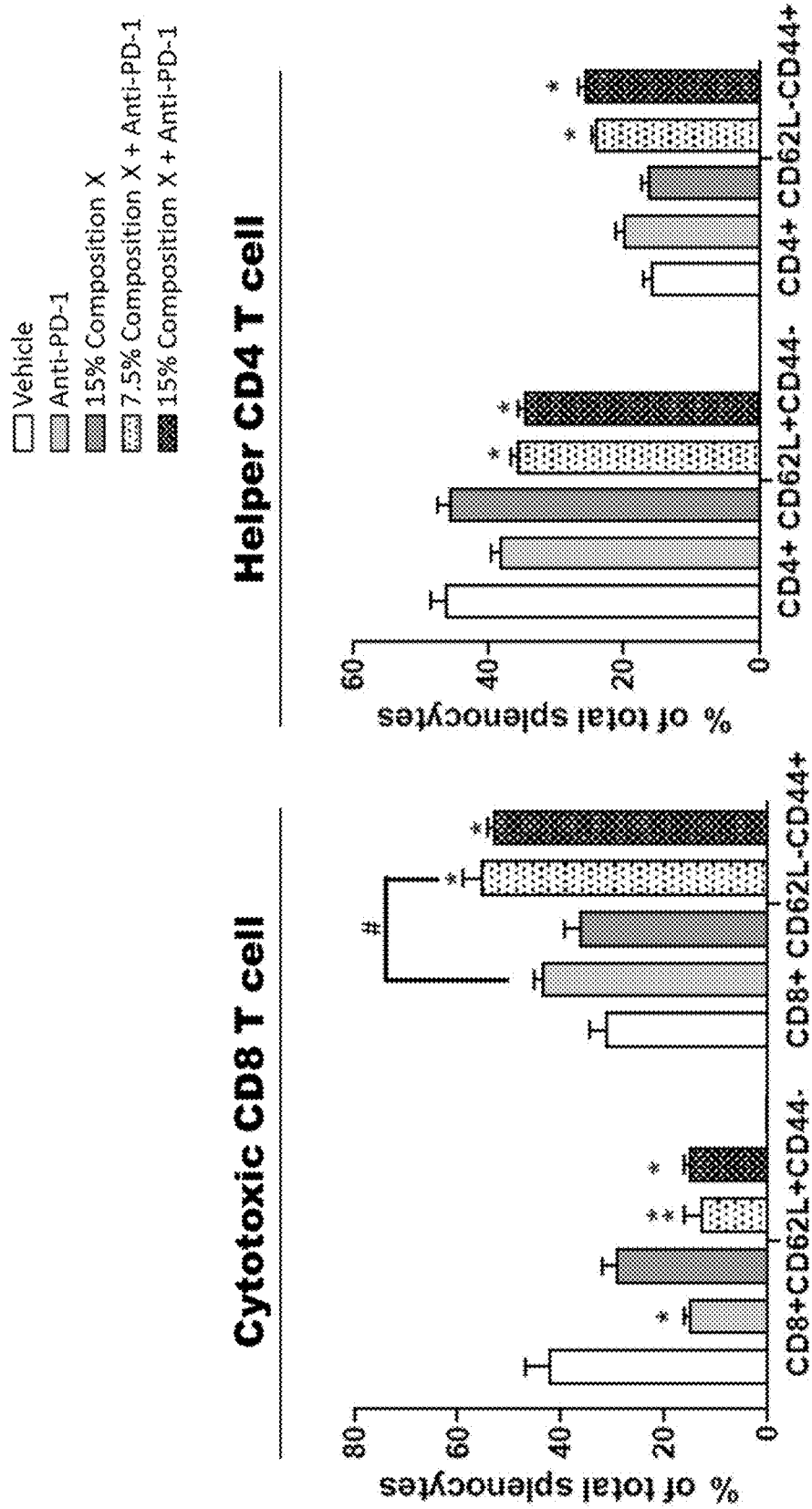
FIG. 9 includes charts showing the effect of Composition X-anti-PD1 combinations on splenic T cell profiling observed in a lung cancer mouse model. *p<0.05; p<0.01; and *p <0.001. P-values were obtained by comparison of each intervention group and the control group (vehicle treated). #p<0.05; ##p<0.01; ###p<0.001. P-values were obtained by comparison of each intervention group and the anti-PD1 antibody-treated group.

The splenic T cell profiling of the mice treated with either the vehicle control or the combinations of anti-PD1 and Composition X was analyzed following the methods described in Example 1 above. As shown in FIG. 9, the percentages of effector memory T cells in both splenic CD8+ and CD4+ cells were significantly increased as a result of the combined treatment of anti-PD1 and Composition X, while naïve T cells decreased as compared with the control.

Figure 10:
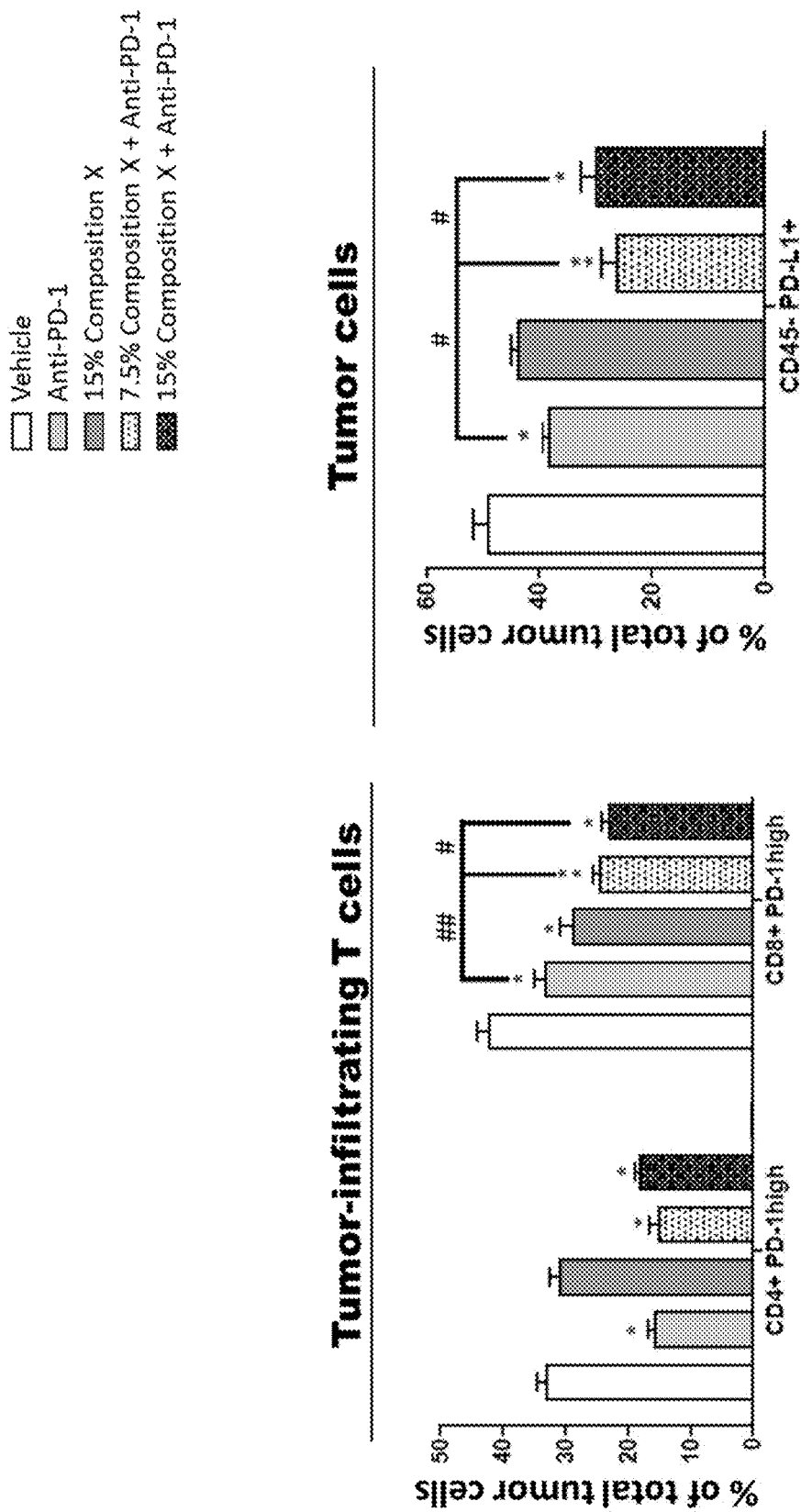
FIG. 10 includes charts showing the PD1/PD-L1 expression profiling in tumor tissues obtained from mice having lung cancer cells transplanted and treated with an anti-PD1 antibody, Composition X, or a combination thereof. *p<0.05; p<0.01; and *p<0.001. P-values were obtained by comparison of each intervention group and the control group (vehicle treated). #p<0.05; ##p<0.01; ###p<0.001. P-values were obtained by comparison of each intervention group and the anti-PD1 antibody-treated group.

Further, the PD1/PD-L1 expression profiling in tumor tissues were analyzed. Tumor-infiltrating PD-1$^{high}$ CD4+ T cells in mice treated with the anti-PD-1 antibody, either taken alone or in combination with Composition X showed similar decreasing trends. Composition X alone decreased tumor-infiltrating PD-1$^{high}$ CD8+ T cells, which is similar (or even better than) the anti-PD-1 antibody. PD-L1 expression in tumor cells was reduced in combination therapy groups as well as (or even better than) in anti-PD-1 group. FIG. 10.

Figure 11:
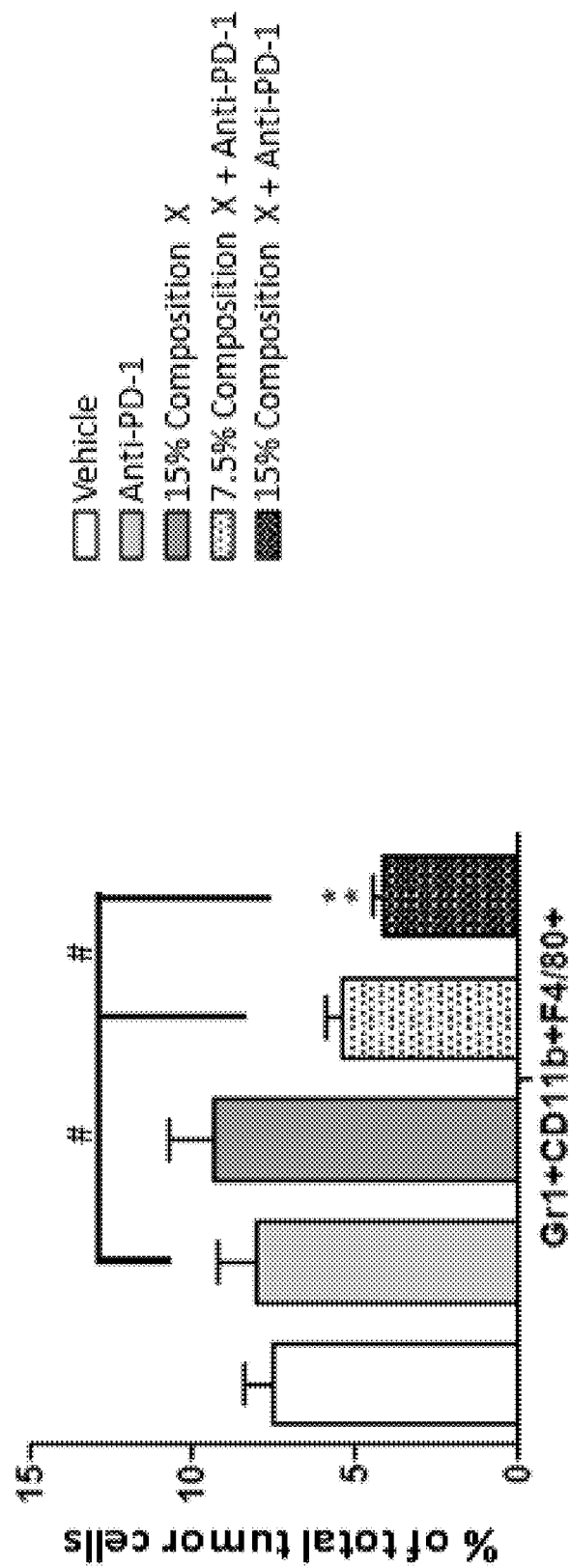
FIG. 11 is a chart showing the tumor-infiltrating myeloid-derived suppressor cells (MDSC) profiling. *p<0.05; p<0.01; and *p<0.001. P-values were obtained by comparison of each intervention group and the control group (vehicle treated). #p<0.05; ##p<0.01; ###p<0.001. P-values were obtained by comparison of each intervention group and the anti-PD1 antibody-treated group.

MDSCs (myeloid-derived suppressor cells) are characterized as Gr-1(+)CD11b(+)F4/80(+) cells. These cells play important roles in tumor development and have a negative effect on tumor immunotherapy. The combined treatment of Composition X and anti-PD-1 significantly decreased the percentage of MDSCs, indicating that this combined therapy would be effective in cancer treatment. FIG. 11.

Example 3: Treating Colon Cancer with an Anti-PD1 Antibody and Composition X Via Intravenous Injection Composition X was prepared following the method described in Example 1 above. The effectiveness of the combined therapy of Composition X, administrated intravenously, and anti-PD1 antibody on colon cancer was investigated in a colon cancer mouse model as follows.

Figure 12:
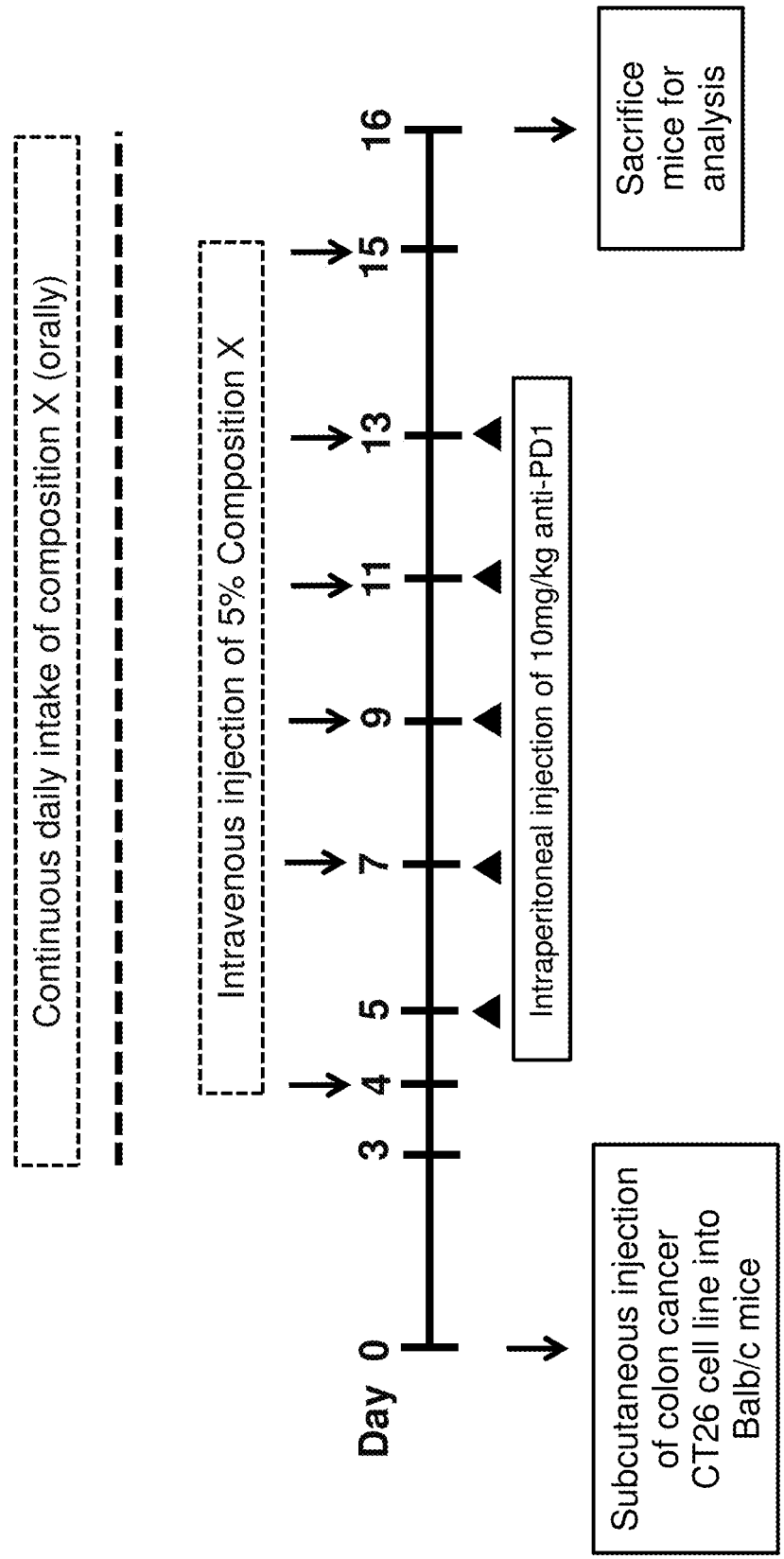
FIG. 12 is a schematic illustration of an experimental design for studying the effect of a combination of an anti-PD1 antibody and a fermented composition (Composition X) via oral administration or intravenous injection in a colon cancer mouse model.

Balb/c mice were injected subcutaneously with $2\times10^5$ colon cancer CT26 cells on Day 0. The mice were injected intraperitoneally with an anti-PD1 antibody at Day 5 at 10 mg/kg when the tumors derived from the grafted colon cancer cells reached an average size of 50 mm$^3$. The injection of the anti-PD1 antibody was repeated at the same dose at Day 7, 9, 11, and 13. The mice were sacrificed at day 16 for analysis. Some of the mice were dosed with 5% diluted Composition X intravenously on day 4, 7, 9, 11, 13, and 15 while some not. A group of mice were administrated with 15% Composition X (10 ml/kg, daily) orally from day 3 until the end of the experiment with or without anti-PD1 injection for comparison. A schematic illustration of this exemplary experimental design is provided in FIG. 12.

Figure 13:
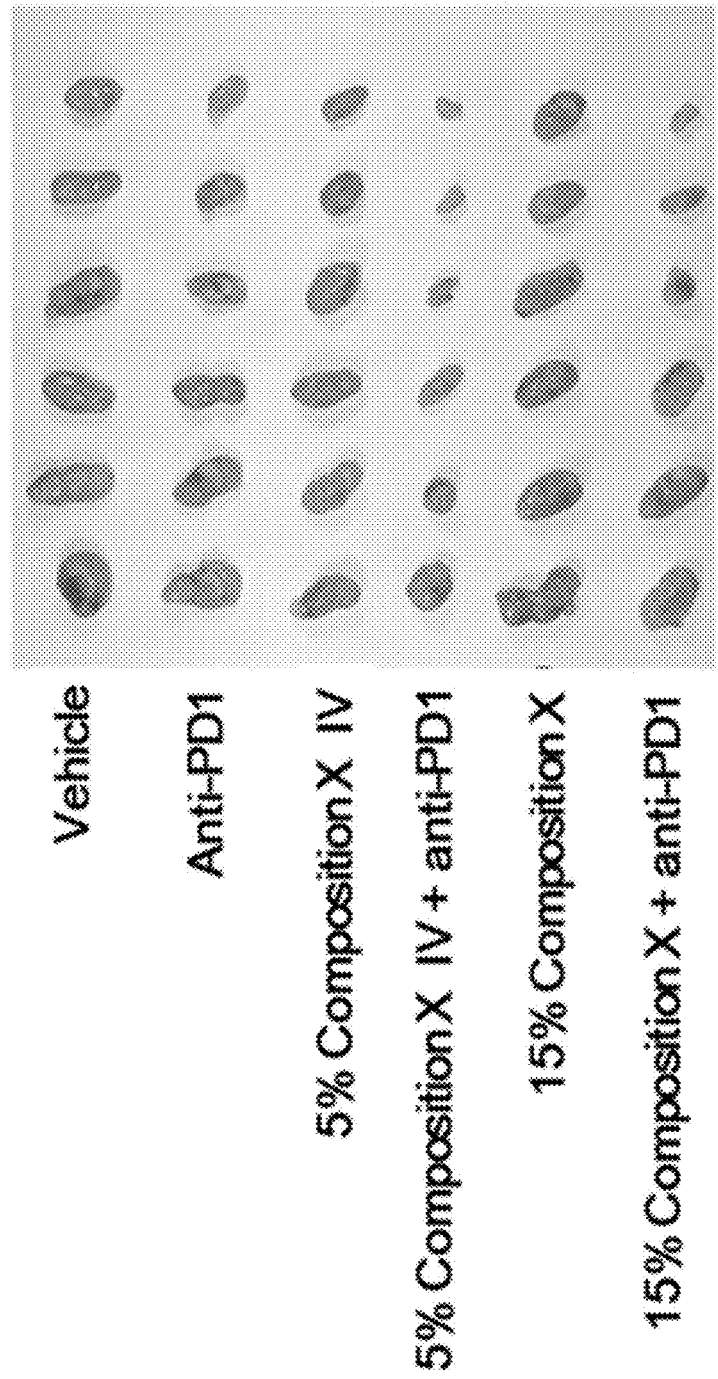
FIG. 13 is a photo showing sizes of tumors formed by subcutaneous injection of colon cancer CT26 cells in mice treated with vehicle control, an anti-PD1 antibody, a combinations of the anti-PD1 antibody and a fermented composition via oral administration, or a combination of the anti-PD1 antibody and the fermented composition via intravenous injection.
Figure 14:
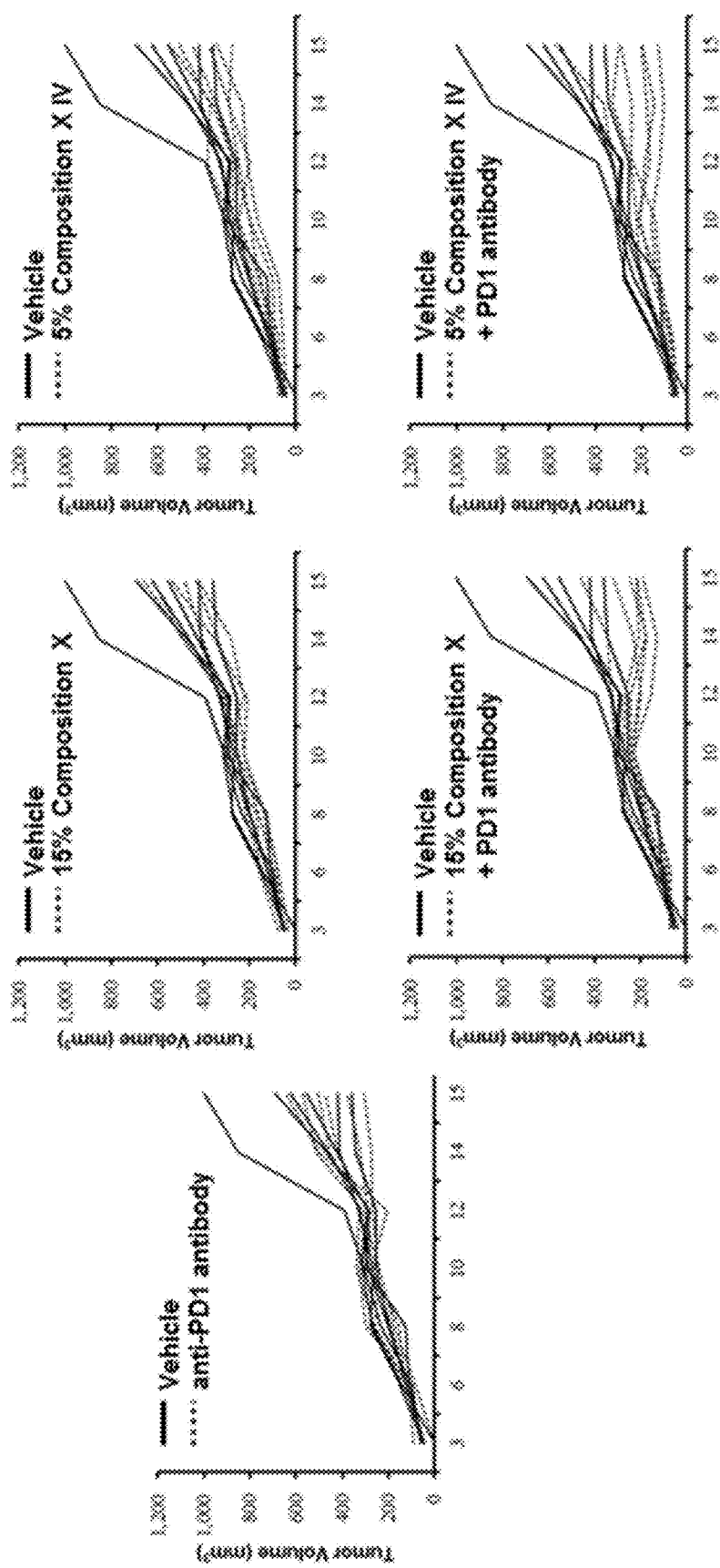
FIG. 14 includes charts showing the inhibitory effects of the anti-PD1/Composition X combination on tumor growth observed in a colon cancer mouse model via either oral administration or intravenous injection.
Figure 15:
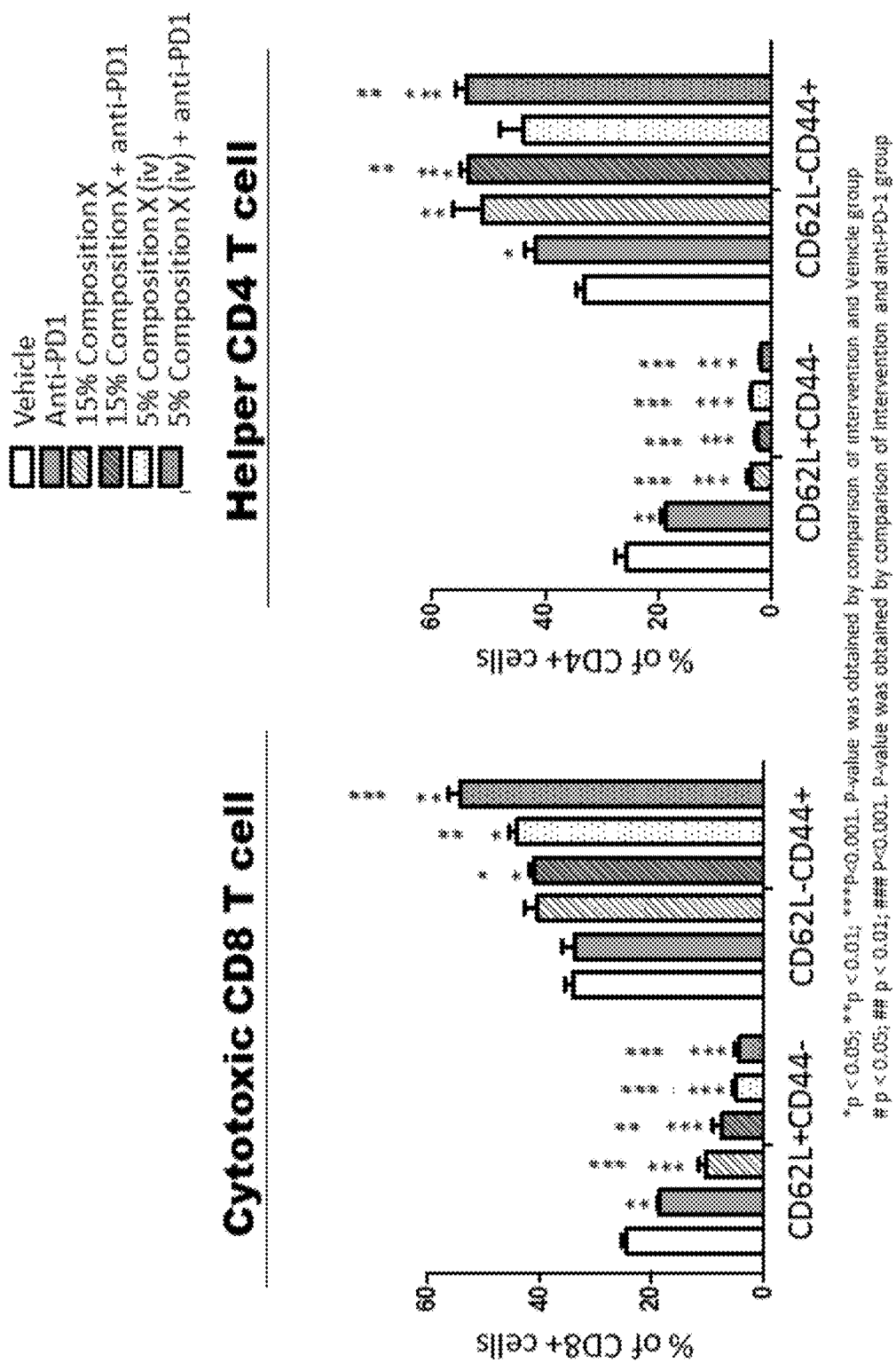
FIG. 15 includes charts showing the effect of Composition X-anti-PD1 combinations on the profiling of T cell at tumor sites observed in a colon cancer mouse model. Composition X was administered either orally or intravenously. *p<0.05; p<0.01; and *p<0.001. P-values were obtained by comparison of each intervention group and the control group (vehicle treated). #p<0.05; ##p<0.01; ###p<0.001. P-values were obtained by comparison of each intervention group and the anti-PD1 antibody-treated group.

As shown in Table 4 below and FIGS. 13 and 14, intravenous administration of Composition X significantly enhances the efficacy of the anti-PD1 antibody in inhibiting tumor growth to a similar extant as oral administration of Composition X. Again, Composition X acted synergistically with the anti-PD1 antibody in suppressing tumor growth.

TABLE 4

Effect of Intravenous Composition X and anti-PD1 Antibody on Tumor Growth in Colon Cancer Mouse Model

| Group (n = 6) | Average Tumor Volume (mm$^3$) | Tumor Growth Inhibition (%) |
|---|---|---|
| Vehicle | 609.5 | — |
| Anti-PD1 | 480.5 | 21.1 |
| 5% Composition X (i.v.) | 415.5 | 31.8 |
| 5% Composition X (i.v.) + anti-PD1 | 282.4 | 53.7 |
| 15% Composition X (p.o.) | 542.3 | 11.0 |
| 15% Composition X (p.o.) + anti-PD1 | 399.9 | 34.4 |

Figure 16:
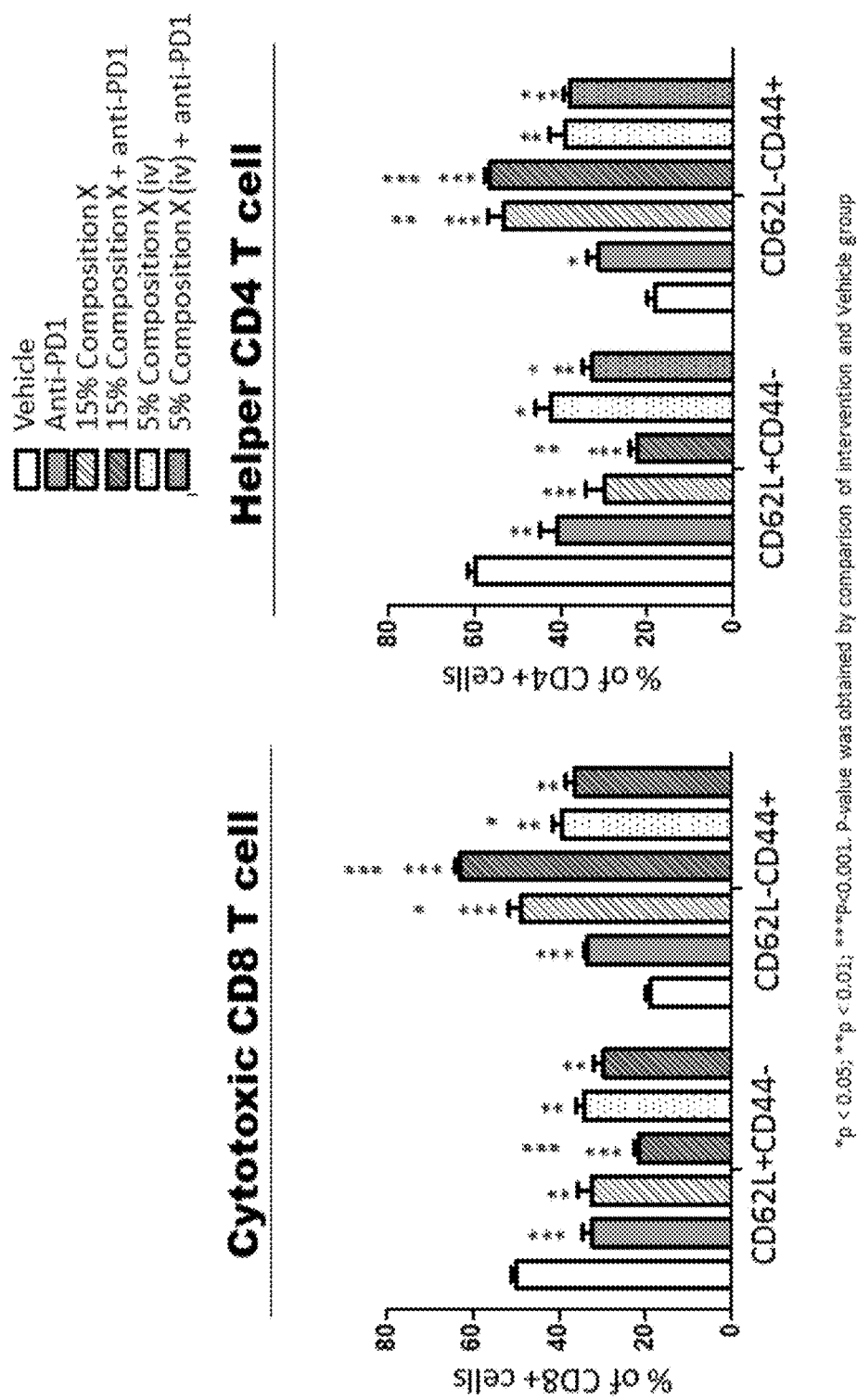
FIG. 16 includes charts showing the effect of Composition X-anti-PD1 combinations on splenic T cell profiling observed in a colon cancer mouse model. Composition X was administered either orally or intravenously. *p<0.05; p<0.01; and *p<0.001. P-values were obtained by comparison of each intervention group and the control group (vehicle treated). #p<0.05; ##p<0.01; ###p<0.001. P-values were obtained by comparison of each intervention group and the anti-PD1 antibody-treated group.
Figure 17:
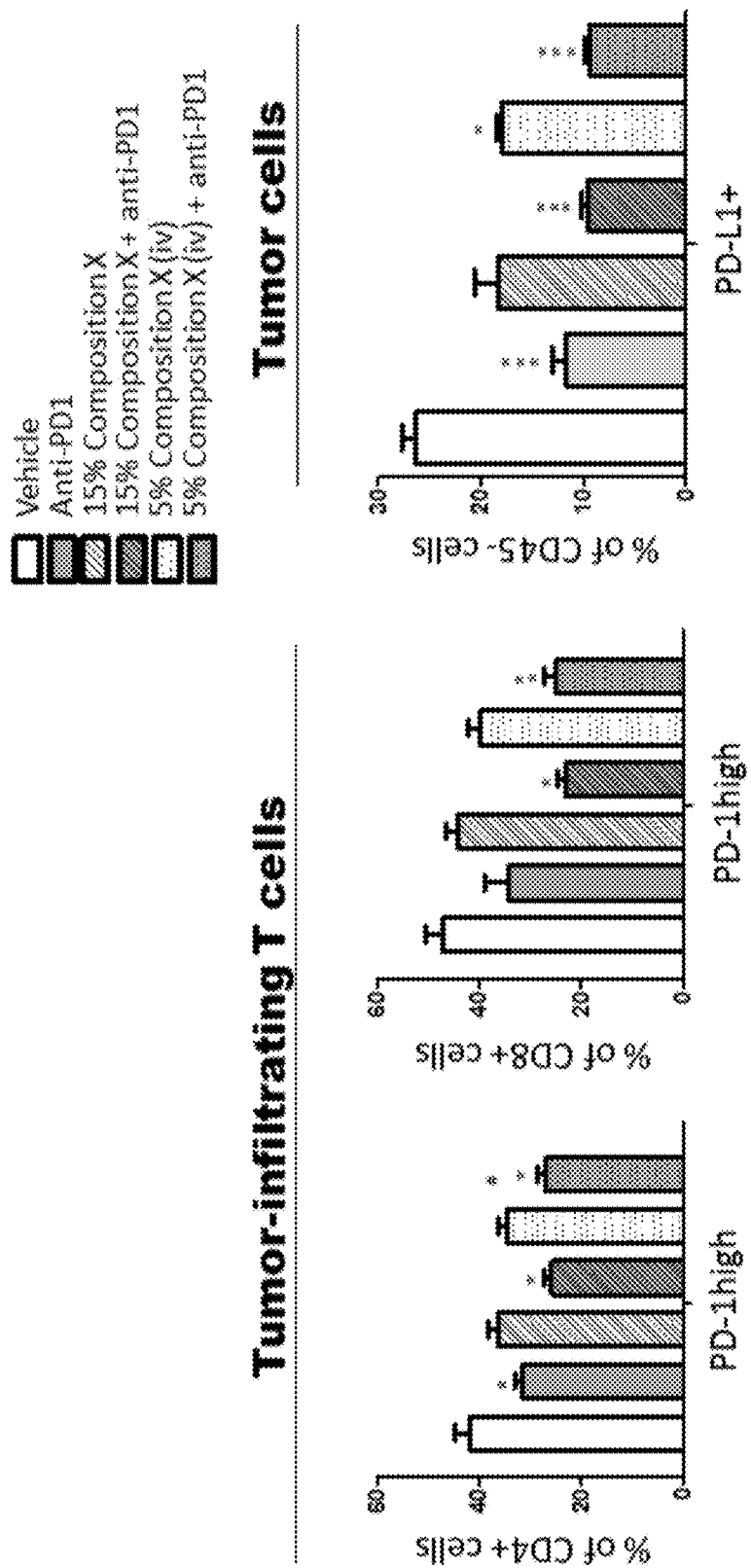
FIG. 17 includes charts showing the PD1/PD-L1 expression profiling in tumor tissues obtained from mice having lung cancer cells transplanted and treated with an anti-PD1 antibody, Composition X, or a combination thereof. Composition X was administered with orally or intravenously. *p<0.05; p<0.01; and *p<0.001. P-values were obtained by comparison of each intervention group and the control group (vehicle treated). #p<0.05; ##p<0.01; ###p<0.001. P-values were obtained by comparison of each intervention group and the anti-PD1 antibody-treated group.
Figure 18:
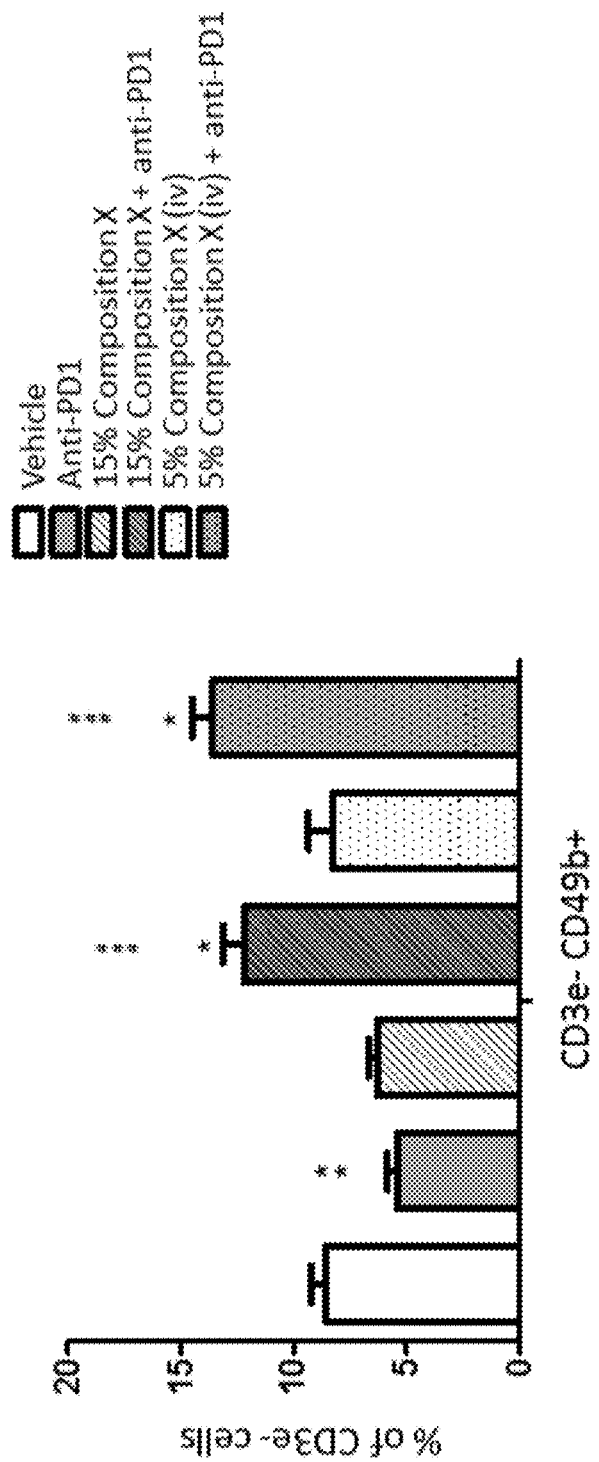
FIG. 18 is a chart showing the effect of an anti-PD1 antibody, Composition X, or a combination thereof on the level of NK cells (characterized as CD3e−/CD49b+). Composition X was administered with orally or intravenously. *p<0.05; p<0.01; and *p<0.001. P-values were obtained by comparison of each intervention group and the control group (vehicle treated). #p<0.05; ##p<0.01; ###p<0.001. P-values were obtained by comparison of each intervention group and the anti-PD1 antibody-treated group.
Figure 19:
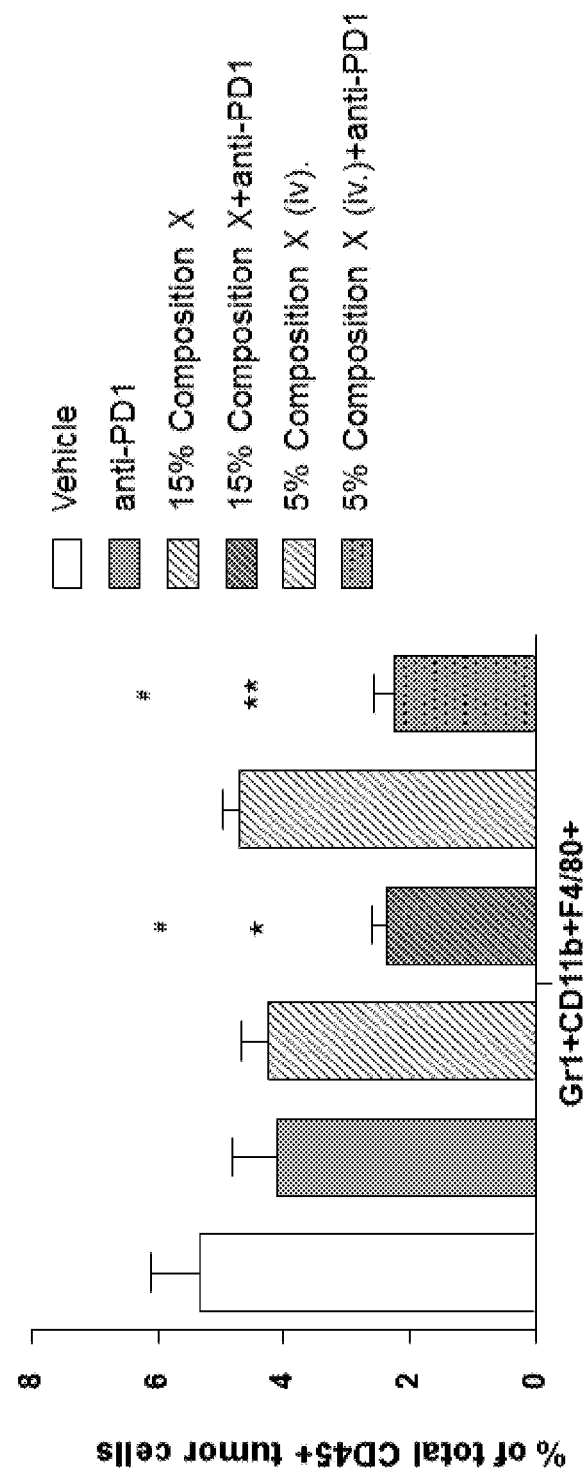
FIG. 19 is a chart showing the tumor-infiltrating myeloid-derived suppressor cells (MDSC) profiling. *p<0.05; p<0.01; and *p<0.001. Composition X was administered with orally or intravenously. P-values were obtained by comparison of each intervention group and the control group (vehicle treated). #p<0.05; ##p<0.01; ###p<0.001. P-values were obtained by comparison of each intervention group and the anti-PD1 antibody-treated group.
Figure 20:
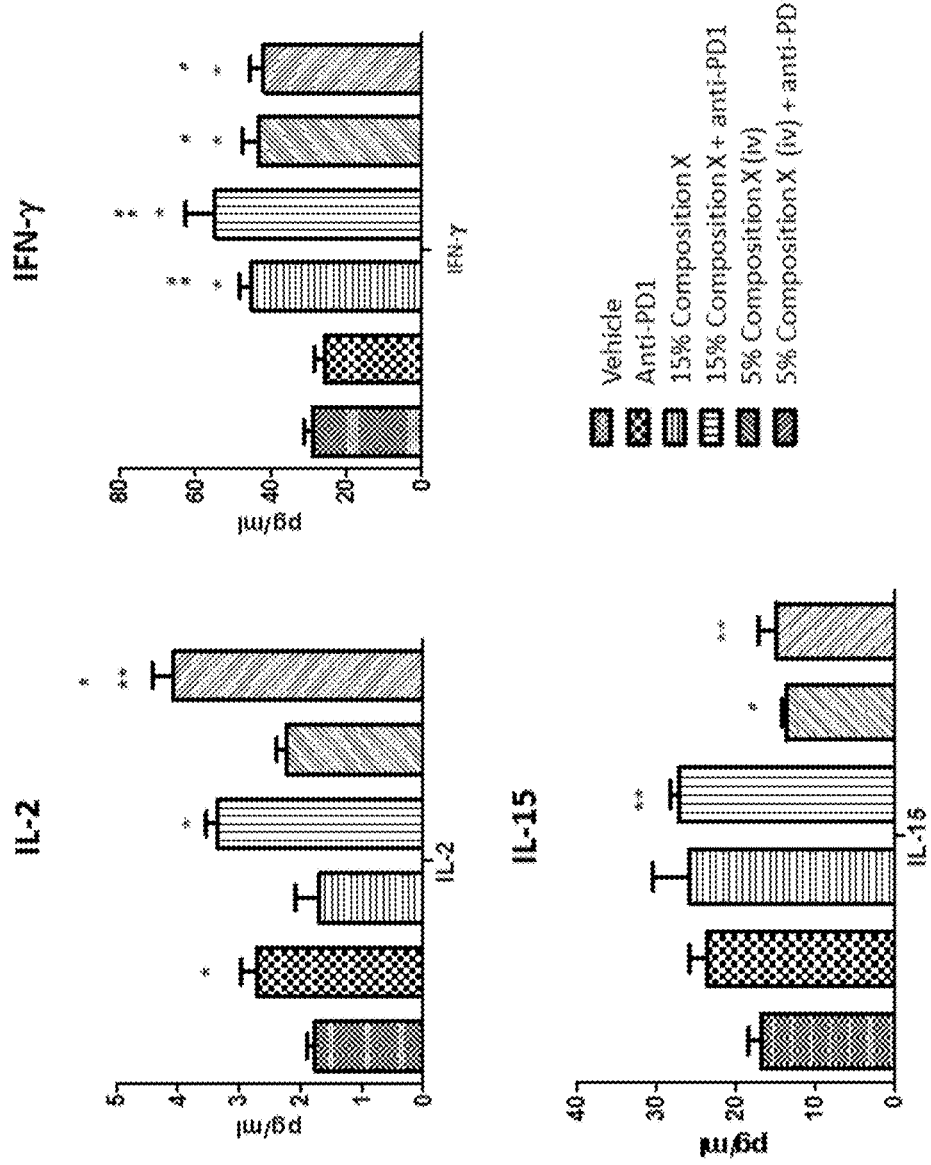
FIG. 20 includes charts showing the level of cytokines IL-2, IFN-γ, and IL-15 at tumor sites in mice treated with a vehicle control, anti-PD1 antibody, Composition X, or a combination thereof. *p<0.05; p<0.01; and *p<0.001. Composition X was administered with orally or intravenously. P-values were obtained by comparison of each intervention group and the vehicle control group. #p<0.05; ##p<0.01; ###p<0.001. P-values were obtained by comparison of each intervention group and the anti-PD1 antibody-treated group.
Figure 21:
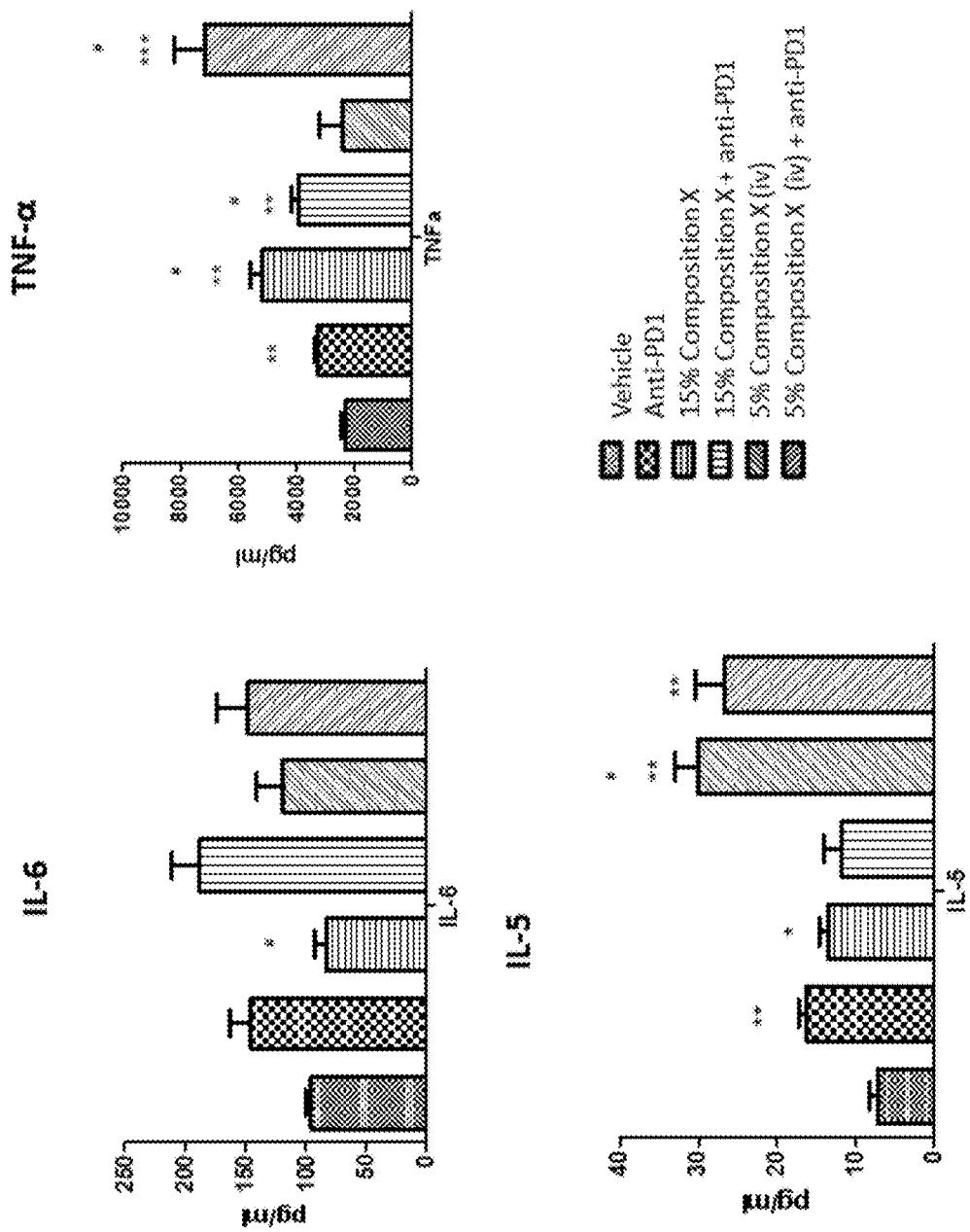
FIG. 21 includes charts showing the level of cytokines IL-6, TNF-α, and IL-5 at tumor sites in mice treated with a vehicle control, anti-PD1 antibody, Composition X, or a combination thereof. *p<0.05; p<0.01; and *p<0.001. Composition X was administered with orally or intravenously. P-values were obtained by comparison of each intervention group and the vehicle control group. #p<0.05; ##p<0.01; ###p<0.001. P-values were obtained by comparison of each intervention group and the anti-PD1 antibody-treated group.
Figure 22:
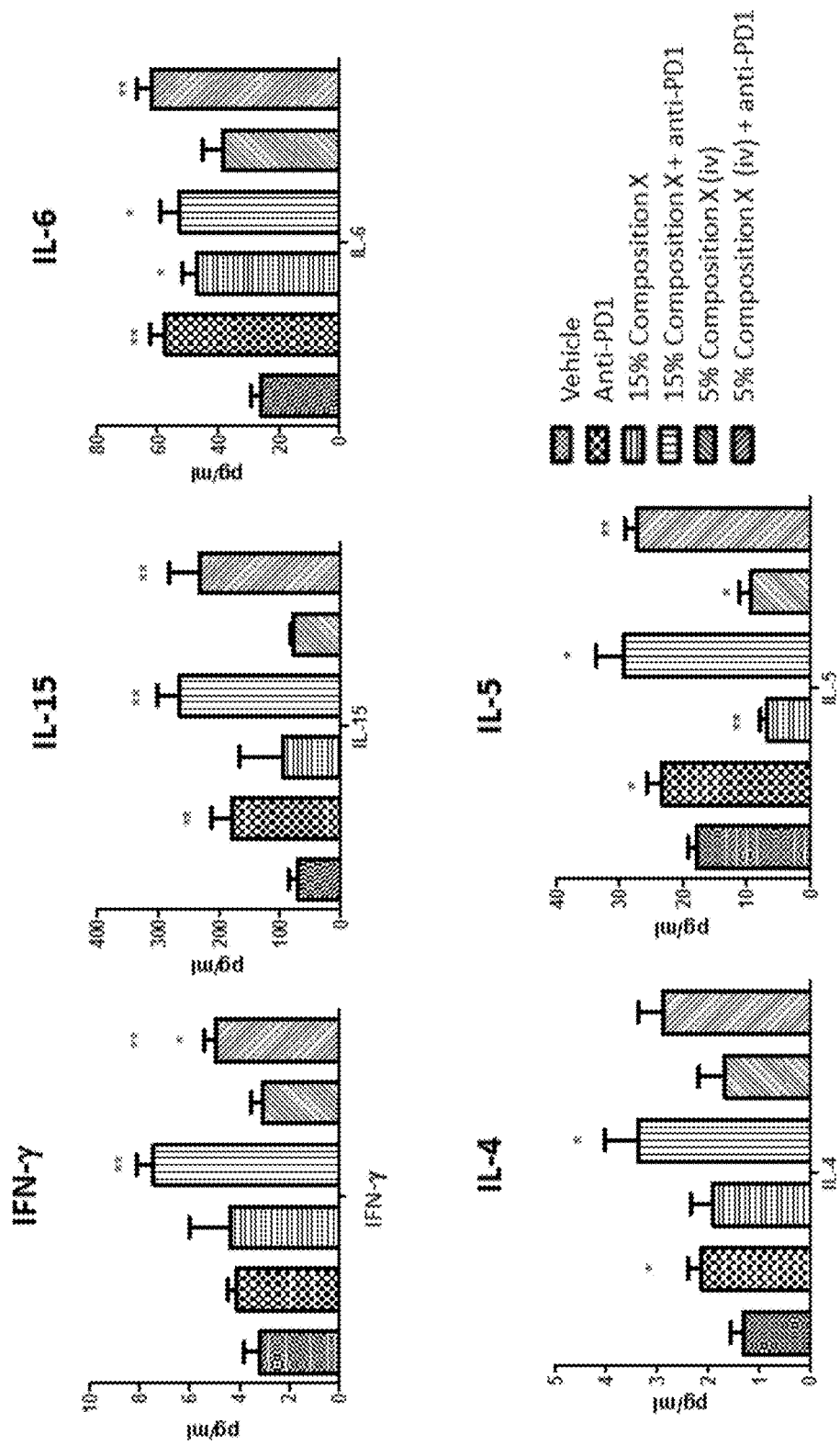
FIG. 22 includes charts showing the serum level of cytokines IFN-γ, IL-15, IL-6, IL-4 and IL-1 in mice treated with a vehicle control, anti-PD1 antibody, Composition X, or a combination thereof. *p<0.05; p<0.01; and *p<0.001. Composition X was administered with orally or intravenously. P-values were obtained by comparison of each intervention group and the vehicle control group.

Immune cell profiling and cytokine expression in the spleen and tumor site were analyzed by flow cytometry (FIGS. 15-22). Again, both the percentage of effector/memory CD4+ and CD8+ T cells significantly increased as a result of combined treatment either by oral or by intravenous administration of Composition X at the tumor sites (FIG. 15), as well as in the spleens (FIG. 16). Further, in both combinations the percentages of PD1$^{high}$ CD4 and CD8 T cells were lower than the control and so was the percentage of PD-L1+ tumor cells (FIG. 17). Similarly, the percentage of NK cells (characterized as CD3e$^-$CD49b$^+$) in the tumors were significantly higher (FIG. 18) while MDSC (characterized as Gr-1$^+$CD11b$^+$F4/80$^+$) were significantly lower (FIG. 19) in both oral and intravenous administration of Composition X combined with anti-PD1.

In addition, cytokine expression profile at the tumor site (FIG. 20-21) as well as in the serum (FIG. 22) was measured. It was observed that both cytokines capable of enhancing T and NK cell functions (IL-2, IFN-γ, IL-15, IL-4) and pro-inflammatory cytokines (IL-5, IL-6, TNF-α) were significantly increased both at the tumor sites and in the serum.

Example 4: Treating Colon Cancer with an Anti-PD1 Antibody and Composition X Changed the Microbiota in the Large Intestine An anti-PD1 antibody and Composition X were given to Balb/c mice transplanted with colon cancer CT26 cells following the procedure illustrated in FIG. 1A. After the treatment, the proximal colon tissues of the treated mice were excised on day 17, wherein the mice were sacrificed and subjected to microbiota analysis with the next generation sequencing technology. The results showed that several of the bacterial species were changed when mice bearing colon cancer were treated with the anti-PD1/Composition X combination as compared to mice bearing colon cancer without any treatment. Exemplary bacterial species were listed in Table 5.

TABLE 5

Effect of Composition X and anti-PD1 Antibody on Changing Microbiota in Mice Bearing Colon Cancer.

| Input Taxon | Average Proportion in Vehicle Group | Average Proportion in anti-PD1 + 15% Composition X Group | Kruskal-Wallis test ($p < 0.05$) |
|---|---|---|---|
| *Streptococcus* | 1.94E−05 | 0 | 0.0277 |
| *Anaeroplasma* | 1.01E−05 | 0 | 0.0277 |
| RF39 | 1.15E−04 | 0 | 0.0277 |
| *Ruminococcus* | 1.78E−04 | 4.68E−05 | 0.0339 |

Figure 23:
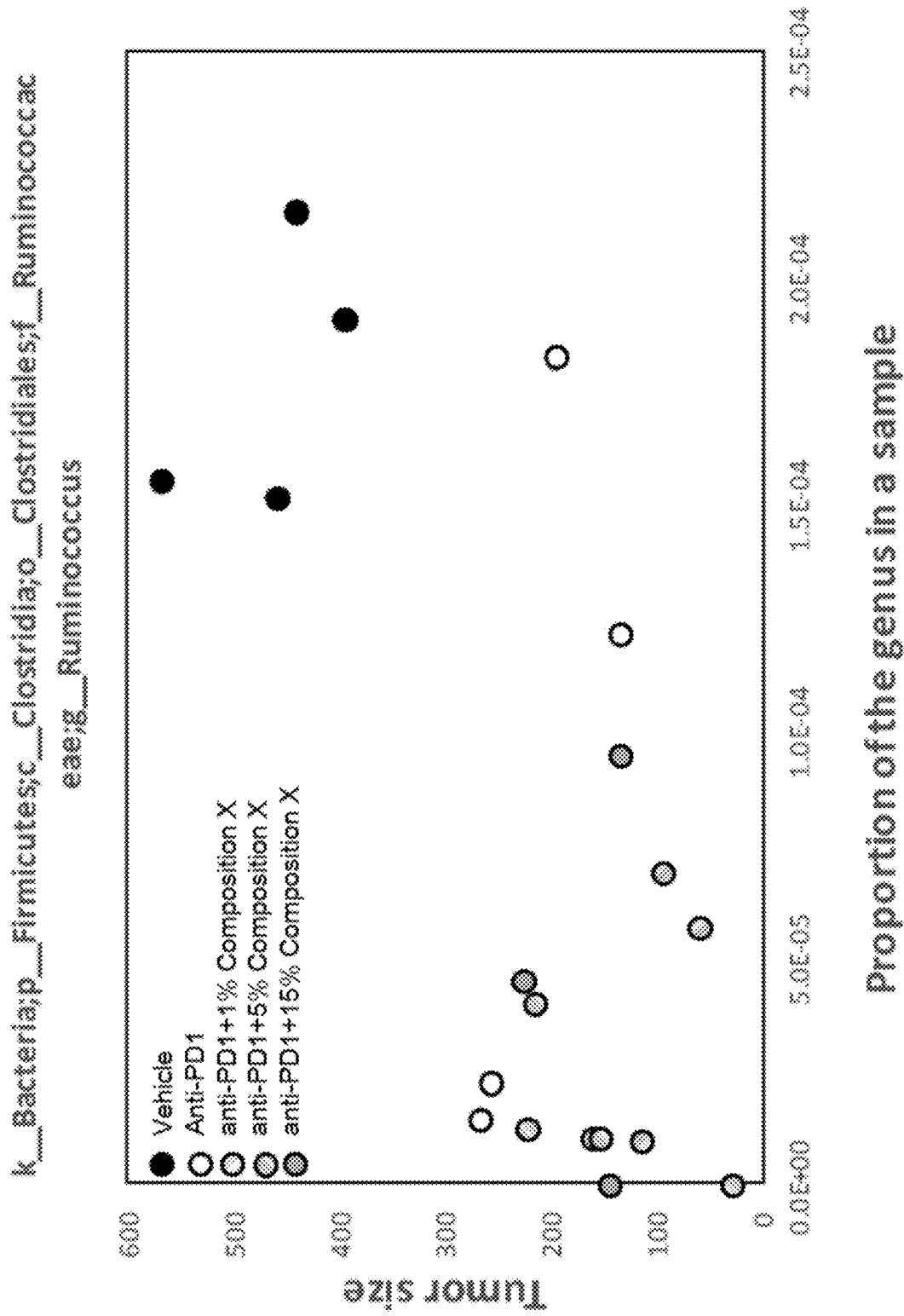
FIG. 23 is a diagram showing the correlation between tumor size and abundance of certain bacteria species in the intestine of mice treated with a vehicle, an anti-PD1 antibody, a fermented soybean composition (Composition X), or a combination of the anti-PD1 antibody and Composition X.

In addition, the abundance of *Ruminococcus* is closely related to the size of the tumor, as shown in FIG. 23, where X-axis represents the abundance of *Ruminococcus* and Y-axis represent the size of the tumor. When the tumor size is bigger, i.e. the tumors in vehicle group, The abundance of *Ruminococcus* in the large intestines of mice having tumors of large size (the mice of the vehicle control group) is much higher than that of mice having tumors of small size (the mice treated by the Composition X/anti-PD1 antibody combination). Since intestinal microbiota was suggested to affect the colon cancer (see, e.g., Gao et. al., *Frontiers in Microbiology*, 6:20, 2015), results obtained from this study indicates that Composition X and/or the anti-PD1 antibody may be effective in treating colon cancer via, inter alia, modulating intestinal microbiota of a subject being treated with this combination.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for treating cancer, comprising:
   (i) administering to a subject in need thereof an effective amount of an immune checkpoint inhibitor, which is an inhibitor of PD-1; and
   (ii) administering to the subject a fermented composition, which comprises multiple metabolites that are generated via fermentation of a legume plant or a portion thereby by a mixture of microorganisms; wherein the legume plant is soybean, and wherein the mixture of microorganisms comprise a yeast and a *lactobacillus*.

2. The method of claim 1, wherein the fermented composition is administered by oral administration or intravenous administration.

3. The method of claim 1, wherein the fermented composition is in liquid form.

4. The method of claim 1, wherein the fermented composition comprises multiple metabolites that are generated via fermentation of an extract of soybean.

5. The method of claim 4, wherein the fermented composition comprises multiple metabolites that are generated via fermentation of the soybean extract by the yeast and the *lactobacillus*.

6. The method of claim 1, wherein the multiple metabolites comprise a combination of lactic acid, acetic acid, and/or 3-aminoisobutyric acid.

7. The method of claim 6, wherein the fermented composition comprises lactic acid at 5-20% by weight, acetic acid at less than 5% by weight, and 3-aminoisobutyric acid at less than 5% by weight.

8. The method of claim 1, wherein the fermented composition is prepared by a process comprising:
(i) growing the yeast and the *lactobacillus* in a medium comprising the legume plant, a portion thereof, or an extract thereof under conditions allowing for fermentation of the legume plant, the portion thereof, or the extract thereof; and
(ii) collecting the fermented composition obtained from step (i).

9. The method of claim 8, wherein the preparation process further comprises filtering the fermented composition obtained from step (ii), sterilizing the fermented composition, and/or concentrating the fermented composition.

10. The method of claim 1, wherein the fermented composition is administered before, after, or concurrently with the administration of the immune checkpoint modulator.

11. The method of claim 1, wherein the inhibitor of PD-1 is an antibody specific to PD-1 or a ligand thereof.

12. The method of claim 11, wherein the antibody is a human antibody, a humanized antibody, or a chimeric antibody.

13. The method of claim 12, wherein the antibody is specific to PD-1.

14. The method of claim 1, wherein the cancer is selected from the group consisting of colon cancer, lung cancer, breast cancer, pancreatic cancer, skin cancer, brain cancer, ovarian cancer, kidney cancer, stomach cancer, head and neck cancer, esophageal cancer, bladder cancer, rectal cancer, bone cancer, uterine cancer, prostate cancer, and hematological malignancy.

15. A method for treating cancer, comprising administering to a subject in need thereof an effective amount of a fermented composition, which comprises multiple metabolites that are generated via fermentation of a legume plant or a portion thereof by a mixture of microorganisms, which comprise a yeast and a *lactobacillus*; wherein the legume plant is soybean, and wherein the subject has undergone or is undergoing an anti-cancer therapy that involves an immune checkpoint inhibitor, which is an inhibitor of PD-1.

16. The method of claim 15, wherein the fermented composition is administered by oral administration or intravenous administration.

17. The method of claim 15, wherein the fermented composition is in liquid form.

18. The method of claim 15, wherein the fermented composition comprises multiple metabolites that are generated via fermentation of an extract of soybean by the yeast and the *lactobacillus*.

19. The method of claim 15, wherein the multiple metabolites comprise a combination of lactic acid, acetic acid, and/or 3-aminoisobutyric acid.

20. The method of claim 19, wherein the fermented composition comprises lactic acid at 5-20% by weight, acetic acid at less than 5% by weight, and 3-aminoisobutyric acid at less than 5% by weight.

21. The method of claim 15, wherein the fermented composition is prepared by a process comprising:
(i) growing the yeast and the *lactobacillus* in a medium comprising the legume plant, the portion thereof, or the extract thereof under conditions allowing for fermentation of the legume plant, the portion thereof, or the extract thereof; and
(ii) collecting the fermented composition obtained from step (i).

22. The method of claim 21, wherein the preparation process further comprises filtering the fermented composition obtained from step (ii), sterilizing the fermented composition, and/or concentrating the fermented composition.

23. The method of claim 15, wherein the inhibitor of PD-1 is an antibody specific to PD-1 or a ligand thereof.

24. The method of claim 23, wherein the antibody is a human antibody, a humanized antibody, or a chimeric antibody.

25. The method of claim 24, wherein the antibody is specific to PD-1.

26. The method of claim 15, wherein the cancer is selected from the group consisting of colon cancer, lung cancer, breast cancer, pancreatic cancer, skin cancer, brain cancer, ovarian cancer, kidney cancer, stomach cancer, head and neck cancer, esophageal cancer, and bladder cancer, rectal cancer, bone cancer, uterine cancer, prostate cancer, and hematological malignancy.

27. The method of claim 1, wherein the cancer is lung cancer or colon cancer.

28. The method of claim 15, wherein the cancer is lung cancer or colon cancer.

* * * * *